(12) United States Patent
Yodfat et al.

(10) Patent No.: US 9,199,031 B2
(45) Date of Patent: Dec. 1, 2015

(54) MAINTAINING GLYCEMIC CONTROL DURING EXERCISE

(76) Inventors: Ofer Yodfat, Maccabim-Reut (IL); Gali Shapira, Haifa (IL); Illai Gescheit, Tel Aviv (IL)

( * ) Notice: Subject to any disclaimer, the term of this patent is extended or adjusted under 35 U.S.C. 154(b) by 587 days.

(21) Appl. No.: 12/810,864

(22) PCT Filed: Dec. 25, 2008

(86) PCT No.: PCT/IL2008/001667
§ 371 (c)(1),
(2), (4) Date: Jul. 8, 2010

(87) PCT Pub. No.: WO2009/081403
PCT Pub. Date: Jul. 2, 2009

(65) Prior Publication Data
US 2010/0286601 A1    Nov. 11, 2010

Related U.S. Application Data

(60) Provisional application No. 61/009,281, filed on Dec. 26, 2007.

(51) Int. Cl.
*A61M 5/14*     (2006.01)
*A61M 5/142*    (2006.01)
(Continued)

(52) U.S. Cl.
CPC .......... *A61M 5/14244* (2013.01); *A61M 5/1723* (2013.01); *G06F 19/3456* (2013.01);
(Continued)

(58) Field of Classification Search
CPC ............... A61M 5/14244; A61M 5/14248; A61M 2005/14208

USPC ............... 604/65–67, 890.1–892.1, 503, 504; 600/316, 347, 365
See application file for complete search history.

(56) References Cited

U.S. PATENT DOCUMENTS 3,771,694 A    11/1973  Kaminski
4,498,843 A    2/1985   Schneider et al.
(Continued)

OTHER PUBLICATIONS

The Diabetes Control and Complications Trial (DCCT) Research Group, "The Effect of Intensive Treatment of Diabetes on the Development and Progression of Long-Term Complications in Insulin-Dependent Diabetes Mellitus", *N Engl J Med* 329: 977-986 (1993).

(Continued)

*Primary Examiner* — Laura Bouchelle
(74) *Attorney, Agent, or Firm* — Dinsmore & Shohl LLP

(57) ABSTRACT

Devices, apparatuses and methods for controlling blood-glucose levels during exercise are described. For example, an insulin infusion apparatus can include a control module to regulate a rate of therapeutic fluid release into a body of a patient based on a determined therapeutic fluid requirement profile, and a dispensing unit to release therapeutic fluid at the regulated rate. The methods and devices can be implemented by receiving a first value corresponding to a first glucose concentration before an exercise activity of a user; receiving a second value corresponding to a second glucose concentration after the exercise activity for the user; determining a glucose concentration change based on a difference between the second value and the first value; modifying a basal rate based on a comparison of the glucose concentration change with a predetermined threshold value; and, recording the modified basal rate in a computer-readable memory device.

48 Claims, 29 Drawing Sheets

(51) Int. Cl.
*A61M 5/172* (2006.01)
*G06F 19/00* (2011.01)

(52) U.S. Cl.
CPC ........ *G06F19/3481* (2013.01); *A61M 5/14248* (2013.01); *A61M 2005/14208* (2013.01); *A61M 2205/056* (2013.01); *A61M 2205/3569* (2013.01)

(56) References Cited

U.S. PATENT DOCUMENTS

| | | | |
|---|---|---|---|
| 4,657,486 | A | 4/1987 | Stempfle |
| 5,957,895 | A | 9/1999 | Sage et al. |
| 6,485,461 | B1 | 11/2002 | Mason et al. |
| 6,572,542 | B1 * | 6/2003 | Houben et al. ................ 600/300 |
| 6,589,229 | B1 | 7/2003 | Connelly et al. |
| 6,723,072 | B2 | 4/2004 | Mahoney et al. |
| 6,740,059 | B2 | 5/2004 | Flaherty et al. |
| 7,935,076 | B2 * | 5/2011 | Estes et al. ...................... 604/65 |
| 2001/0039374 | A1 * | 11/2001 | Schulman ...................... 600/300 |
| 2003/0212379 | A1 * | 11/2003 | Bylund et al. ................. 604/504 |
| 2005/0065464 | A1 * | 3/2005 | Talbot et al. .................... 604/66 |
| 2005/0090726 | A1 * | 4/2005 | Ackerman ..................... 600/347 |
| 2005/0107676 | A1 * | 5/2005 | Acosta et al. .................. 600/316 |
| 2006/0263839 | A1 * | 11/2006 | Ward et al. ....................... 435/14 |
| 2007/0032706 | A1 * | 2/2007 | Kamath et al. ................ 600/300 |
| 2007/0106218 | A1 | 5/2007 | Yodfat et al. |
| 2007/0191702 | A1 * | 8/2007 | Yodfat et al. .................. 600/365 |
| 2008/0103447 | A1 * | 5/2008 | Reggiardo et al. ............ 604/131 |
| 2008/0214916 | A1 | 9/2008 | Yodfat et al. |
| 2008/0215035 | A1 | 9/2008 | Yodfat et al. |
| 2009/0171589 | A1 * | 7/2009 | Kovatchev ....................... 702/19 |
| 2010/0057043 | A1 * | 3/2010 | Kovatchev et al. ........... 604/504 |
| 2010/0298764 | A1 * | 11/2010 | Yodfat et al. .................... 604/66 |
| 2011/0160652 | A1 | 6/2011 | Yodfat et al. |

OTHER PUBLICATIONS

The Diabetes Control and Complications Trial/Epidemiology of Diabetes Interventions and Complications (DCCT/EDIC) Study Research Group, "Intensive Diabetes Treatment and Cardiovascular Disease in Patients with Type 1 Diabetes", N Engl J Med 353 (25): 2643-53 (2005).

Perkins et al., "Type 1 Diabetes and Exercise: Using the Insulin Pump to Maximun Advantage", *Canadian Journal of Diabetes* 30(1): 72-29 (2006).

UK Prospective Diabetes Study (UKPDS) Group, Intensive Blood-Glucose Control with Sulphonylureas or Insulin Compared with Conventional Treatment and Risk of Complications in Patients with Type 2 Diabetes (UKPDS 33), The Lancet 352: 837-853 (1998).

UK Prospective Diabetes Study (UKPDS) Group, "Tight Blood Pressure Control and Risk of Macrovascular and Microvascular in Type 2 Diabetes: UKPDS 38", BMJ 317, (7160): 703-13 (1998).

\* cited by examiner

APPROXIMATE GRAMS OF CARB USED PER HOUR IN DIFFERENT EXERCISES

| ACTIVITY | GRAMS OF CARB USED PER HOUR | | |
|---|---|---|---|
| WT: | 100 LBS. | 150 LBS. | 200 LBS. |
| BASEBALL | 25 | 38 | 50 |
| BASKETBALL | | | |
| MODERATE | 35 | 48 | 61 |
| VIGOROUS | 59 | 88 | 117 |
| BICYCLING | | | |
| 6 MPH | 20 | 27 | 34 |
| 10 MPH | 35 | 48 | 61 |
| 14 MPH | 60 | 83 | 105 |
| 18 MPH | 95 | 130 | 165 |
| 20 MPH | 122 | 168 | 214 |
| RACING | 75 | 112 | 149 |
| DANCING | | | |
| MODERATE | 17 | 25 | 33 |
| VIGOROUS | 28 | 43 | 57 |
| DIGGING | 45 | 65 | 83 |
| EATING | 6 | 8 | 10 |
| GOLFING | | | |
| PULLCART | 23 | 35 | 46 |
| HANDBALL | 59 | 88 | 117 |
| JUMP ROPE 80/MIN | 73 | 109 | 145 |
| MOPPING | 16 | 23 | 30 |
| MOUNTAIN CLIMBING | 60 | 90 | 120 |
| PAINTING | | | |
| INSIDE | 14 | 20 | 28 |
| OUTSIDE | 21 | 31 | 42 |
| RAKING LEAVES | 19 | 28 | 38 |
| RUNNING | | | |
| 5 MPH | 45 | 68 | 90 |
| 8 MPH | 96 | 145 | 190 |
| 10 MPH | 126 | 189 | 252 |
| SHOVELLING | 31 | 45 | 57 |
| SKATING | | | |
| MODERATE | 25 | 34 | 43 |
| VIGOROUS | 67 | 92 | 117 |
| SKIING | | | |
| CROSSCNTRY-5 MPH | 76 | 105 | 133 |
| DOWNHILL | 52 | 72 | 92 |
| WATER | 42 | 58 | 74 |
| SOCCER | 45 | 67 | 89 |
| SWIMMING | | | |
| SLOW CRAWL | 41 | 56 | 71 |
| FAST CRAWL | 69 | 95 | 121 |
| TENNIS | | | |
| MODERATE | 23 | 34 | 45 |
| VIGOROUS | 59 | 88 | 117 |
| VOLLEYBALL | | | |
| MODERATE | 23 | 34 | 45 |
| VIGOROUS | 59 | 88 | 117 |
| WALKING | | | |
| 3 MPH | 15 | 22 | 29 |
| 4.5 MPH | 30 | 45 | 59 |

FIG 1

| Exercise Duration | Exercise Intensity | | | | | | | | |
|---|---|---|---|---|---|---|---|---|---|
| | Mild | | | Moderate | | | Intense | | |
| | Carbs* | Bolus | Basal | Carbs* | Bolus | Basal | Carbs* | Bolus | Basal |
| 15 min | + 0g | normal | normal | + 0g | normal | normal | + 20g | - 10% | normal |
| 30 min | + 10g | normal | normal | + 20g | - 10% | normal | + 40g | - 20% | normal |
| 45 min | + 18g | - 10% | normal | + 30g | - 20% | normal | + 50g | - 30% | normal |
| 60 min | + 25g | - 15% | normal | + 40g | - 30% | - 20% | + 60g | - 40% | - 10% |
| 90 min | + 38g | - 20% | normal | + 55g | - 45% | - 20% | + 90g | - 50% | - 20% |
| 120 min | + 50g | - 30% | normal | + 70g | - 60% | - 20% | + 110g | - 70% | - 30% |
| 240 min | + 80g | - 50% | - 10% | + 120g | - 60% | - 20% | + 200g | - 70% | - 40% |

FIG 2

| BORG SCALE | EFFORT INTENSITY |
|---|---|
| 6 | 20% EFFORT - VERY, VERY LIGHT (REST) |
| 7 | 30% EFFORT |
| 8 | 40% EFFORT |
| 9 | 50% EFFORT - VERY LIGHT - GENTLE WALKING |
| 10 | 55% EFFORT |
| 11 | 60% EFFORT - FAIRLY LIGHT |
| 12 | 65% EFFORT |
| 13 | 70% EFFORT - MODERATELY HARD - STEADY PACE |
| 14 | 75% EFFORT |
| 15 | 80% EFFORT – HARD |
| 16 | 85% EFFORT |
| 17 | 90% EFFORT - VERY HARD |
| 18 | 95% EFFORT |
| 19 | 100% EFFORT - VERY, VERY HARD |
| 20 | EXHAUSTION |

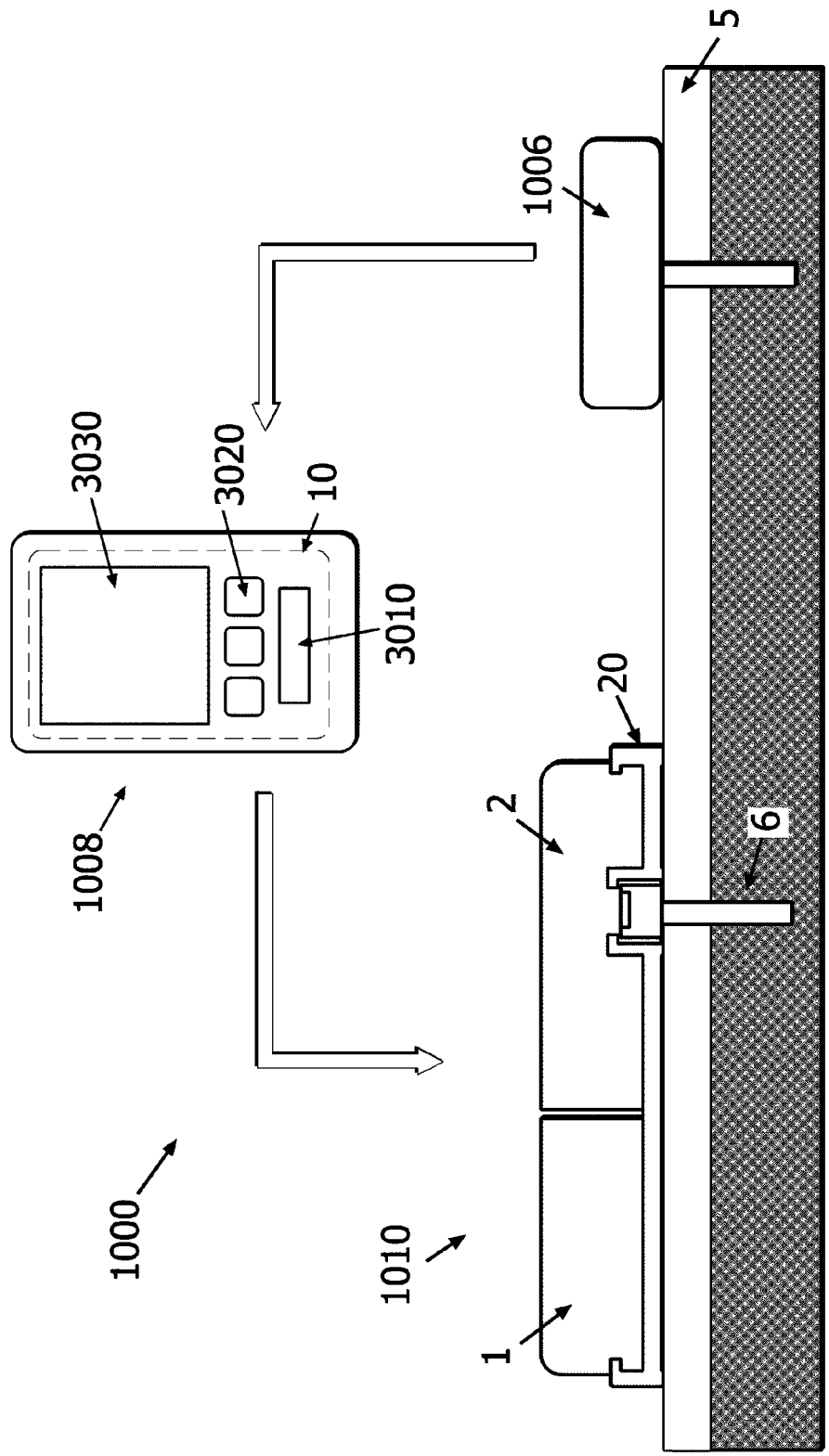

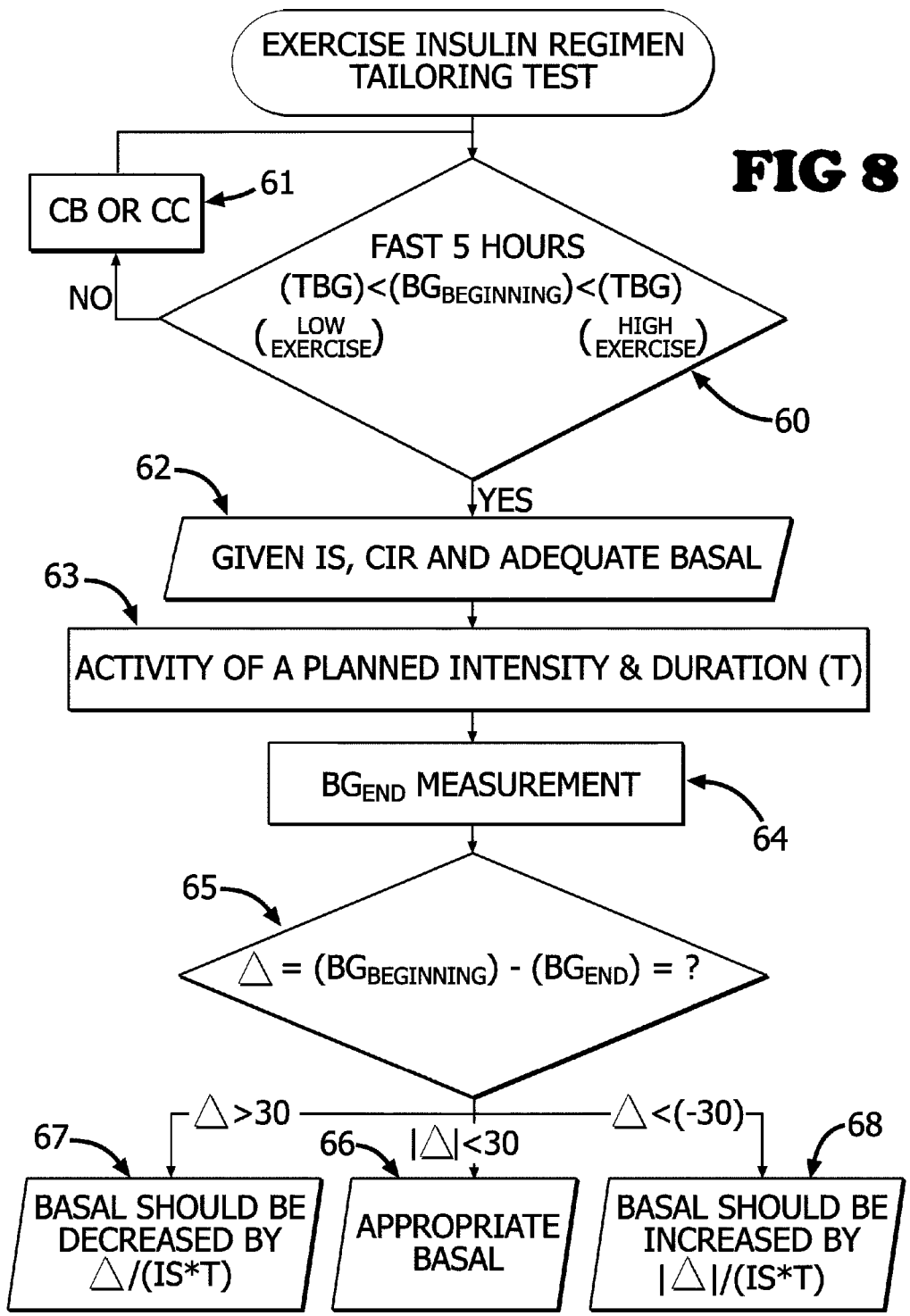

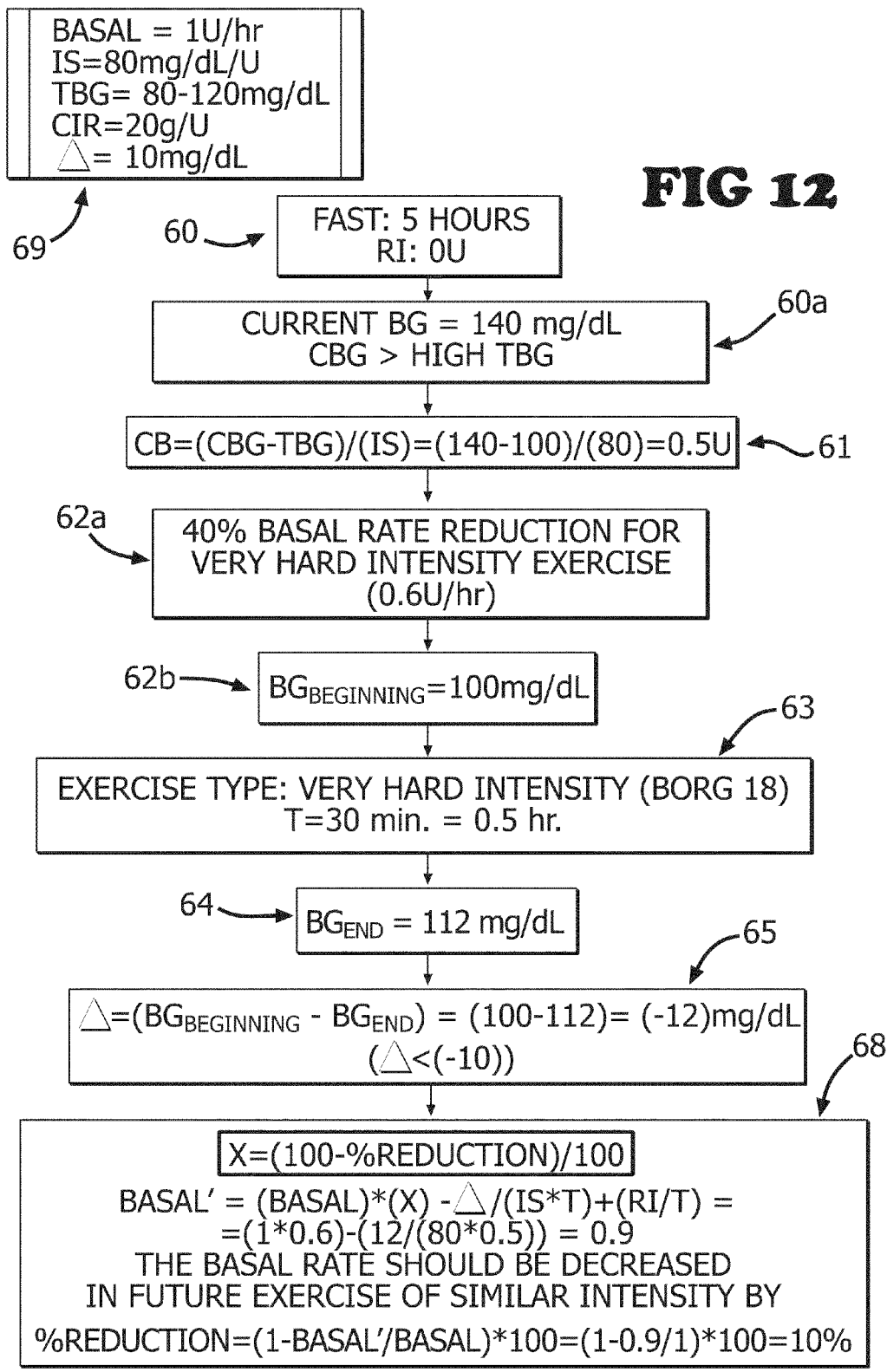

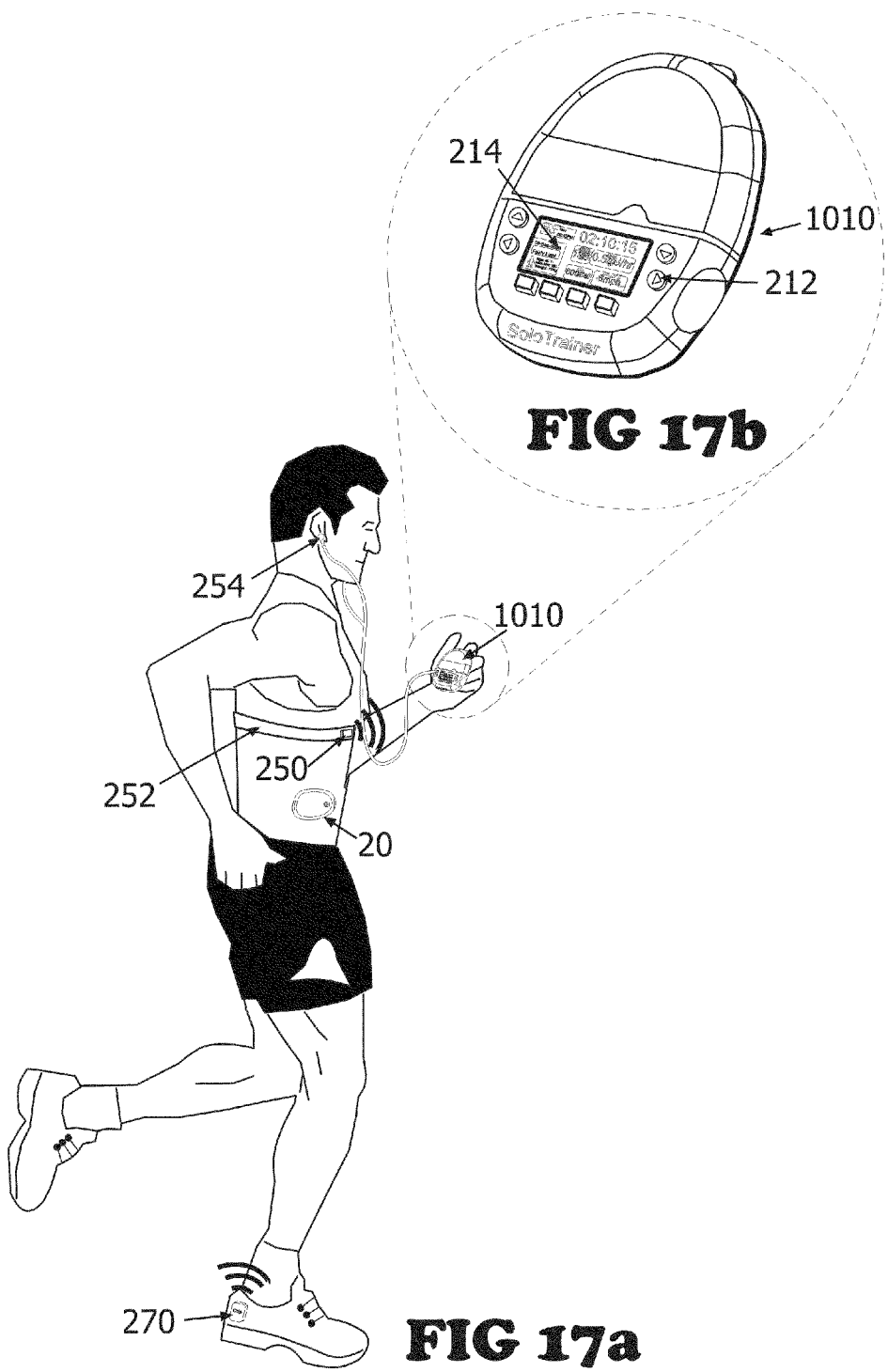

MAINTAINING GLYCEMIC CONTROL DURING EXERCISE

CROSS-REFERENCE TO RELATED APPLICATIONS

This application claims priority to International Patent Application No. PCT/IL2008/001667, Published as PCT Publication No. WO 2009/081403, to Ofer Yodfat et al., filed Dec. 25, 2008, and entitled "MAINTAINING GLYCEMIC CONTROL DURING EXERCISE", which claims priority to U.S. Provisional Application Ser. No. 61/009,281 filed Dec. 26, 2007, the contents of all of which are hereby incorporated by reference in their entireties.

FIELD

The present disclosure relates generally to sustained infusion of insulin and to methods for maintaining glycemic control during exercise. More particularly, the present disclosure relates to insulin dispensing patch systems that can continuously monitor bodily glucose levels and methods for achieving glycemic control during exercise.

BACKGROUND

Diabetes mellitus is a disease of major global importance, increasing in frequency at almost epidemic rates, such that the worldwide prevalence in 2006 is currently at 170 million people and is predicted to at least double over the next 10-15 years. Diabetes is characterized by a chronically raised blood glucose concentration (hyperglycemia), due to a relative or absolute lack of the pancreatic hormone, insulin. Within the healthy pancreas, beta cells, located in the islets of Langerhans, continuously produce and secrete insulin according to the blood glucose levels, maintaining near constant glucose levels in the body.

Much of the burden of the disease to the user and to healthcare resources is due to the long-term tissue complications, which affect both the small blood vessels (microangiopathy, causing eye, kidney and nerve damage) and the large blood vessels (causing accelerated atherosclerosis, with increased rates of coronary heart disease, peripheral vascular disease and stroke). The Diabetes Control and Complications Trial (DCCT) demonstrated that development and progression of the chronic complications of diabetes are greatly related to the degree of altered glycemia as quantified by determinations of glycohemoglobin (HbAlc). [see, DCCT Trial, N Engl J Med 1993; 329: 977-986, UKPDS Trial, Lancet 1998; 352: 837-853. BMJ 1998; 317, (7160): 703-13 and the EDIC Trial, N Engl J Med 2005; 353, (25): 2643-53]. Thus, maintaining normoglycemia by frequent glucose measurements and adjustment of insulin delivery is of utmost importance.

Frequent insulin administration can be done by multiple daily injections (MDI) with syringe or by continuous subcutaneous insulin injection (CSII) with insulin pumps. In recent years, ambulatory portable insulin infusion pumps have emerged as a superior alternative to multiple daily injections of insulin, liberating patients from repeated self-administered injections, and allowing greater flexibility in dose administration.

Insulin pumps can deliver rapid acting insulin 24 hours a day through a catheter placed under the skin. The total daily insulin dose can be divided into basal and bolus doses. Basal insulin can be delivered continuously over 24 hours, and can keep the blood glucose levels in range between meals and overnight. Diurnal basal rates can be pre-programmed or manually changed according to various daily activities.

Insulin boluses can be delivered before meals to counteract carbohydrates loads or during episodes of high blood sugar levels. The amount of insulin in the administered bolus can depend on several parameters:

Amount of carbohydrates (Carb) to be consumed, alternatively defined as "serving", wherein 1 serving=15 grams of Carbohydrates;

Carbohydrate-to-insulin ratio (CIR), i.e. the amount of carbohydrate balanced by one unit of insulin;

Insulin sensitivity (IS), i.e. the amount of blood glucose value lowered by a unit of insulin;

Current blood glucose levels (CBG; "BG"—blood glucose);

Target blood glucose levels (TBG), i.e. the desired blood glucose levels. TBG for most people suffering from diabetes is in the range of 90-130 mg/dL before a meal, and less than 180 mg/dL 1-2 hours after the start of a meal;

Residual insulin, i.e. the amount of insulin remaining from recent boluses that is still working.

Several ambulatory insulin infusion devices are currently available on the market. The first generation of portable insulin pump was a "pager like" device attached to a user's belt. The first generation device included a reservoir within the device housing. A long tube delivered insulin from the pump attached to a user's belt to a remote insertion site. Such first generation devices are disclosed in U.S. Pat. Nos. 3,771,694, 4,657,486, and 4,498,843. The first generation devices were uncomfortable, bulky devices with a long tube. Consequently, these first generation devices were rejected by the majority of diabetic insulin users because the devices impacted regular activities, such as sports and swimming. In addition, the long delivery tube excluded some optional remote insertion sites, like the buttocks and the extremities.

To avoid the tubing limitations, another concept, of second generation, was proposed. This next concept included a housing having a bottom surface adapted for contact with the patient's skin, a reservoir disposed within the housing, and an injection needle adapted for communication with the reservoir. These skin adhered devices could be disposed of every 2-3 days like current pump infusion sets. For example, this paradigm was described by Schneider, in U.S. Pat. No. 4,498,843, Burton in U.S. Pat. No. 5,957,895, Connelly, in U.S. Pat. No. 6,589,229, and by Flaherty in U.S. Pat. No. 6,740,059. Other configuration of skin adhered pumps are disclosed in U.S. Pat. Nos. 6,723,072 and 6,485,461. In these patents the pump is composed of one piece and adheres to the patient skin for the entire usage duration. The needle emerges from the bottom surface of the device and is fixed to the device housing. These second-generation skin adhered devices tend to be expensive, bulky and heavy.

The pump/infusion device described in US published Patent Application No. 20070106218 and in the U.S. Provisional Patent Application No. 61/123,509, the contents of which are hereby incorporated by reference in their entireties, is a miniature portable programmable fluid dispenser that has no tubing and can be attached to the patient skin. It is composed of two parts, a disposable part and a reusable part. After connection of the reusable and the disposable parts, the unified device presents a thin profile. The reusable part contains the electronic and driving mechanism, and the disposable part contains reservoir delivery tube and an exit port. In some implementations, the device comprises a remote control unit that can allow data acquisition, programming, and user inputs.

Exercise is a therapeutic tool for people with diabetes. Exercise can increase lifespan and reduce the risk of cardiovascular diseases. However, the physiology of BG regulation during exercise is quite complex, leading to poor glycemic control and/or a decrease in active lifestyle among people with diabetes. BG levels during exercise can depend on a balance between glucose mobilization from the liver and muscle and glucose consumption by the working muscles. For example, when glycogen storage is depleted, fat stores can be accessed for lipolysis.

In the setting of inappropriately high insulin concentration during exercise, hepatic glucose output can be inhibited and unopposed glucose disposal into active muscle can cause hypoglycemia. Hypoglycemia may occur during exercise or be delayed by up to 24-36 hours post-exercise. People with diabetes who suffer from hypoglycemia-associated autonomic failure may be affected from exercise induced hypoglycemia more frequently and more profoundly, creating a vicious cycle of hypoglycemia unawareness.

In the setting of inappropriately low insulin levels or excessive counter-regulatory hormone release (e.g. cortisol, catecholamines), hepatic glucose output can be excessive thus leading to hyperglycemia and potential ketoacidosis. (Canadian Journal of Diabetes 2006; 30(1):72-79).

SUMMARY OF THE EMBODIMENTS

Methods and devices for modifying insulin basal rate delivery are provided. Devices, systems and methods for tailoring an insulin delivery regimen (e.g., basal rate delivery, bolus delivery, or a combination thereof; hereinafter referred to as "test", or "evaluation") for achieving better glycemic control during and around exercise time is described herein. In some implementations, a method for tailoring an insulin delivery regimen may be based on exercise intensity, exercise type, exercise duration, starting time blood glucose levels, and exercise starting time residual insulin (RI). For example, glycemic control during and around exercise time can be achieved by manipulation of the pump's basal insulin delivery, recommended consumption of carbohydrates, or a combination of the two. The glycemic control can be achieved by regulating therapeutic fluid release (e.g., release of insulin) into the body by regulating one or more of a rate of a release of the therapeutic fluid, an amount of therapeutic fluid released into the body, a duration of release of the therapeutic fluid.

The methods and devices can be implemented by receiving a first value corresponding to a first glucose concentration before an exercise activity of a user; receiving a second value corresponding to a second glucose concentration after the exercise activity for the user; determining a glucose concentration change based on a difference between the second value and the first value; modifying a basal rate based on a comparison of the glucose concentration change with a predetermined threshold value; and, recording the modified basal rate in a computer-readable memory device.

For example, modifying the basal rate can comprises decreasing the basal rate by $$\frac{\Delta}{IS*T}$$

for insulin delivery to the user based on a determination that the glucose concentration change in the user is greater than the predetermined threshold value, wherein $\Delta$ represents the glucose concentration change, IS represents insulin sensitivity of a user and T represents a duration of the exercise activity.

The basal rate can also be modified by increasing the basal rate by $|\Delta|/(IS*T)$ based on a determination that the glucose concentration change is less than a negative predetermined threshold value, wherein $\Delta$ represents the glucose concentration change, IS represents insulin sensitivity of a user and T represents a duration of the exercise activity.

In some implementations, the methods and devices can also be implemented by instructing a user to fast prior to the exercise activity and/or reducing the basal rate prior to the exercise activity by a change basal factor corresponding to a schedule of physical activity intensity levels.

Modifying the basal rate can comprise decreasing the basal rate by (basal−X*Basal)−$\Delta$/(IS*T) based on a determination that the glucose concentration change is greater than the predetermined threshold value, wherein $\Delta$ represents the glucose concentration change, IS represents insulin sensitivity of a user, T represents a duration of the exercise activity, X represents the change basal factor and Basal represents the basal rate.

Alternatively, modifying the basal rate can comprise increasing the basal rate by (basal−X*basal)+$|\Delta|$/(IS*T) based on a determination that the glucose concentration change is less than a negative predetermined threshold value, wherein $\Delta$ represents the glucose concentration change, IS represents insulin sensitivity of a user, T represents a duration of the exercise activity, X represents the change basal factor and Basal represents the basal rate.

In some embodiments, a user interface for receiving data can be provided. The data can be relating to the schedule of physical activity intensity levels. At least a portion of the data from the schedule of physical activity levels can be selected based on a physiological parameter of the user. For example, the physical parameter can be a heart rate determined based on a signal received from a heart rate monitor. The heart rate can also be determined based on a signal provided by a sensor installed in an article of footwear.

In some aspects, the methods and devices can be implemented by providing a user interface adapted for receiving a first set of inputs, the first set of inputs comprising at least one of a fasting period, an IS, a TBG, an RI and a CIR; providing a user interface adapted for receiving a second set of inputs, the second set of inputs comprising at least one of a pre-exercise body glucose level, an exercise intensity level, an exercise duration, a post-exercise body glucose level; invoking a processor to determine a basal rate modification data based on the first set of inputs and the second set of inputs; and, transforming the basal rate modification data into at least one of a visual depiction, an audible announcement, and a vibrational notification. For example, the exercise intensity level corresponds to a schedule of physical activity intensity levels. The basal rate delivery can be adjusted in response to a confirmation received from the user.

In some aspects, the methods and devices can be implemented by receiving a physiological parameter of the user; invoking a processor to determine a modified basal rate based on the physiological parameter; transmitting a signal comprising the modified basal rate to a user interface device, the signal further comprising at least one of the physiological parameter, a body glucose data, exercise intensity level data; transforming at least a portion of the signal into at least one of a visual depiction, an audible announcement, and a vibrational notification.

For example, the physiological parameter can be received wirelessly, the signal can be transmitted wirelessly, the user interface device can be a watch, PDA or a remote control. The visual depiction can represent a number displayed on a monitor of the user interface device. The visual depiction can represent a graph displayed on a monitor of the user interface device. The graph can correspond to a change in at least one of the physiological parameter, the body glucose data, the basal rate data and exercise intensity level data over time. The user interface device can be a set of headphones. The user interface device can be adapted to receive a confirmation from a user. For example, the confirmation received from the user can be audible. In some embodiments, the schedule of physical activity intensity levels is a Borg scale.

The methods and devices can further be implemented by modifying the basal rate based on one or more user-specific factors selected from the group consisting of IS, TBG, and RI. The basal rate can be modified upon termination of the exercise activity based on a predetermined configuration, the predetermined configuration can be selected from at least one of a basal rate prior to the exercise activity, a basal rate preprogrammed by the user, or a new basal rate manually selected by the user after the exercise activity.

In some implementations, a recommendation for the user can be generated corresponding to a food adjustment based on the glucose concentration change, and/or, corresponding to an exercise activity based on the glucose concentration change. The modified basal rate can be presented to the user in a form of a percent of the basal rate prior to the modification. The modified basal rate can also be presented to the user in a form of a number of units of insulin.

The user interface device can be a remote control coupled to a dedicated arm strap. The user interface device can also be selected from a group consisting of a personal computer, a PDA or a watch. The user interface device can comprises an opening adapted for receiving a blood test strip. The insulin can be delivered to the user according to the modified basal rate and/or measuring at least one of the first glucose concentration and the second glucose concentration by a continuous glucose monitor (CGM).

Some aspects of the methods and devices described herein can be implemented by receiving a value corresponding to a physical activity intensity level of the user; retrieving from a computer readable memory device a basal rate factor corresponding to the value, the basal rate factor computed based on the physical activity intensity level and one or more user-specific factors; and, adjusting the insulin basal rate delivery for the user based on the basal rate factor.

The user-specific factors can be selected from the group consisting of IS, TBG, and RI. A processor can also be invoked to initiate delivery of insulin to the user based on the modified basal rate. The basal rate delivery adjustment can be carried out without a confirmation received from the user. The physiological parameter can correspond to at least one of a heart rate, a ventilation rate, a body temperature, steps of the user per period of time.

The fluid delivery device can include, for example, a dispensing patch unit and, in some embodiments, a remote control unit which can communicate with the dispensing patch unit and can enable programming of therapeutic fluid delivery, user input and data acquisition. In some embodiments, programming can be carried out manually by operating buttons located on the dispensing patch unit. In some embodiments, the dispensing patch unit can be composed of two parts—a disposable part and a reusable part. The disposable part can contain a reservoir and outlet port which can be provided with connecting lumen and in some preferred embodiments electrical connectors. The reusable part can contain electronics (PCB, processor, etc), driving mechanism and metering portion.

In some embodiments, a cradle unit can be provided which can be a flat sheet that adheres to the skin and allows patch disconnection and reconnection upon patient discretion. After attachment of the cradle unit to the skin, a cannula can be inserted into the subcutaneous compartment through a dedicated passageway ("well") in the cradle unit. Cannula insertion can be done manually or automatically (with inserter) using a sharp tip penetrating member that can be retracted after skin pricking. After insertion the cannula can be rigidly connected to the cradle unit. During connection of patch and cradle units the connecting lumen pierces a self-sealable rubber septum at the upper portion of the cannula and allows fluid communication between the reservoir and the cannula. The described fluid delivery device can comprise a tailored exercise-related insulin regimen feature which enables maintenance of glycemic control during exercise.

BRIEF DESCRIPTION OF THE DRAWINGS

FIG. 1 illustrates a table estimating an amount of carbohydrates used per hour in different exercises.

FIG. 2 illustrates a table for estimating carbohydrate and insulin adjustments needed to balance exercise per 100 lbs.

FIGS. 7a-b illustrate embodiments of an exemplary insulin infusion device including continuous subcutaneous glucose monitors that are configured to provide blood glucose readings for the exercise glycemic control feature.

FIG. 8 is a block diagram representing one implementation of the algorithm of the exercise glycemic control feature.

FIG. 12 provides another exemplary algorithm for the exercise glycemic control feature.

FIGS. 17a-c illustrate a sample detachable patch unit of the insulin dispensing device.

DETAILED DESCRIPTION OF THE EMBODIMENTS

Figures 3, 4:
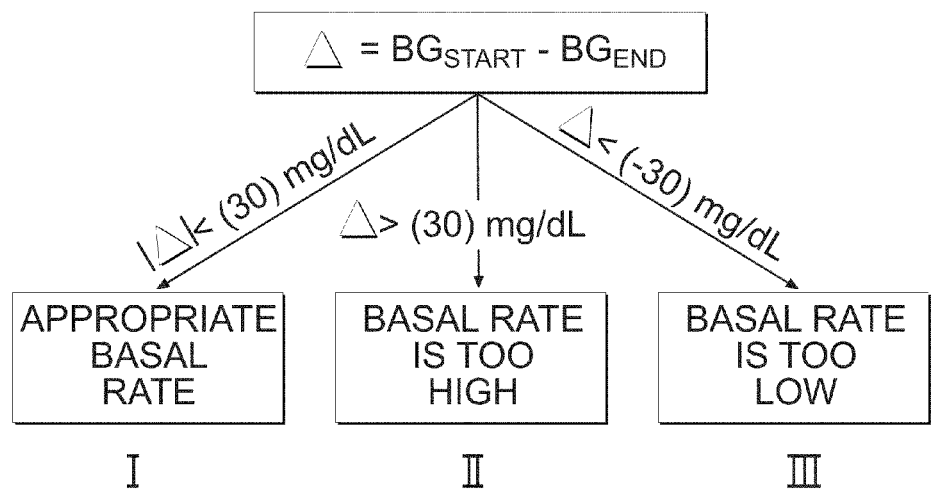
FIG. 3 illustrates the Borg scale of intensity level score.
FIG. 4 provides a flow diagram for basal rate evaluation corresponding to a change in blood glucose concentration.

Devices, systems and methods for tailoring an insulin delivery regimen (e.g., basal rate delivery, bolus delivery, or a combination thereof; hereinafter referred to as "test", or "evaluation") for achieving better glycemic control during and around exercise time is described herein. In some implementations, a method for tailoring an insulin delivery regimen may be based on exercise intensity, exercise type, exercise duration, starting time blood glucose levels, and exercise starting time residual insulin (RI). For example, glycemic control during and around exercise time can be achieved by manipulation of the pump's basal insulin delivery, recommended consumption of carbohydrates, or a combination of the two. The glycemic control can be achieved by regulating therapeutic fluid release (e.g., release of insulin) into the body by regulating one or more of a rate of a release of the therapeutic fluid, an amount of therapeutic fluid released into the body, a duration of release of the therapeutic fluid.

In some embodiments, the methods and devices can be implemented by receiving a first value corresponding to a first glucose concentration before an exercise activity of a user; receiving a second value corresponding to a second glucose concentration after the exercise activity for the user; determining a glucose concentration change based on a difference between the second value and the first value; modifying a basal rate based on a comparison of the glucose concentration change with a predetermined threshold value; and, recording the modified basal rate in a computer-readable memory device.

In some embodiments, the patient can be asked to abstain from food for a period of time, for example, minutes or hours (e.g. 5 hours) and rest before the test. This period can be helpful to reduce the influence of residual insulin (RI). Alternatively, fasting may not be required and the RI can be considered in the evaluation.

In some implementations, the evaluation of glycemic control during an exercise activity can begin by measuring the blood glucose (BG) of the user. In some implementations, the user may be allowed to proceed with the test if the user's BG level is within a pre-exercise target range. (e.g. 90-150 mg/dL). If the user's BG is not within the target range, the user may be asked to administer a correction bolus dose or ingest glucose until target range value is obtained.

The methods described herein may be implemented in an insulin dispensing device (e.g., an insulin pump). The methods may also be implemented in a glucose monitoring device, and/or in a device that can both deliver insulin and monitor glucose levels. Such a device may be capable of delivering insulin automatically or semi-automatically according to sensed glucose levels (e.g., a closed, semi closed or open loop system).

The disclosed methods for tailoring a user, exercise-related insulin regimen can be implemented in an insulin dispensing device that may include an insulin dispensing patch unit. Such an insulin dispensing device may also be part of a system that includes a remote control unit where the disclosed methods may also be implemented. In such unit, a glucose sensing apparatus (e.g. glucometer) can be integrated in the remote control unit and/or within a portion of the insulin dispensing device. The dispensing unit may be a patch unit that can include at least two parts: a reusable part that contains all electronic and driving components (i.e. relatively expensive components) and a disposable part that contains insulin reservoir and other inexpensive components. Thus, preferably, the glucose sensing apparatus may alternatively be integrated in the reusable part of the infusion patch unit of the device.

The methods described herein (including the method for tailoring for a user an exercise-related insulin regimen) may be implemented in a dispensing patch unit as described above, that continuously (for example) senses and monitors body glucose concentration levels and can concomitantly deliver insulin into the body. The dispensing patch unit may include a reusable part and a disposable part, whereby the methods may be implemented within the reusable part. The insulin dispensing and glucose sensing capabilities can be combined into a semi-closed loop system, where a processor-controller apparatus controls the dispensing of basal insulin based on the sensed glucose concentration.

There are several factors that can affect the BG during exercise. For example, the intensity and duration of exercise, and whether exercise is aerobic or anaerobic. The more strenuous an activity, the more likely the BG will drop. Similarly, the longer the activity lasts, the higher the probability that the BG will drop. For example, in anaerobic exercise, a rapid increase in insulin may be required to accommodate the rapid glucose release into the blood. In aerobic exercise, the glucose depletion can exceed glucose production thereby requiring insulin level reduction.

Additional factors may include the user's training level (the more trained a user is, the less insulin reduction required, partially because training can build glycogen stores in the muscles involved), stress hormone release in competitive sports (insulin counter-regulatory hormones), type of exercise (when muscles not typically involved are activated, greater reduction in insulin can be required), and timing of exercise relative to recent meals.

In order to prevent a drop in BG and to maintain normoglycemic levels, the diabetic person may take one of three optional measures: consume extra carbohydrates (hereinafter known as "Excarbohydrates" or "Excarb(s)"), adjust insulin consumption, combine insulin reduction with extra carbohydrate consumption.

When excarbs are consumed, three approaches are possible. One approach is to consume 15-30 grams of carbohydrates every 30-60 minutes of mild to moderate intensity exercise. A second, more quantitative approach is based on body mass, wherein 1 g/kg/h is recommended to account for the drop in BG in mild to moderate intensity exercise. A third, more accurate approach is based on body mass, duration, and intensity of exercise, as depicted in tables such as the table depicted in FIG. 1 published on http://www.diabetesnet.com/diabetes_control_tips/table1.php. Consumption of extra carbohydrates before exercise may pose a problem because meals eaten before and during high intensity sports may cause abdominal discomfort and nausea.

Adjustment of insulin can eliminate the need to consume excessive carbohydrates. The Excarb amount can be translated from grams of carbohydrates to units of insulin by way of the carbohydrate to insulin ratio (CIR). (Excarb/CIR=Insulin amount to be reduced).

One approach is to decrease the insulin from the food bolus dose of a meal preceding exercise. This approach is not favored when meals are remote from activity or when activity is prolonged. Another approach is to decrease the insulin from the basal insulin. This approach is enabled with the use of the insulin pump. The basal rate can also be decreased in an even more general, non-user specific manner according to the physical activity intensity level. This decrease in the basal rate can be adjusted by the user, as a temporary basal rate, prior to exercise. In some implementations, the basal rate may be decreased by the user based on a schedule of physical activity intensity levels. For example, the basal rate may be adjusted based on the Borg scale: 5% change basal factor reduction for a very light intensity exercise (e.g. levels 9-10), 10% change basal factor reduction for a light intensity exercise (e.g. levels 11-12), 20% change basal factor reduction for a moderately hard intensity (e.g. levels 13-14), 30% change basal factor reduction for a hard intensity exercise (e.g. levels 15-16), 40% change basal factor reduction for a very hard intensity exercise (e.g. levels 17-18), and 50% change basal factor reduction for a "very very hard intensity" (e.g. levels 19-20). Yet another approach is to combine the insulin reduction with the extra carbohydrate consumption, for example, as depicted in the table in FIG. 2, published on http://www.diabetesnet.com/diabetes_control_tips/table1.php. The above mentioned approaches are based on set tables and are thus limited to a discrete number of results. In addition, the table-based approaches described above overlook user-specific parameters (e.g. insulin absorption rate, training level) and, thus, may not be accurate.

In some implementations, the method can assist the user in determining the intensity of the planned exercise activity. For example, the table in FIG. 3 illustrates one scale of exercise intensity levels (a.k.a. Borg scale). The example of the Borg scale in FIG. 3 was published on http://www.healthnewengland.com/healthydirections/Health_Articles/exercise/Exercise_intensity.html. In some embodiments, the user can select activity intensity level based on individual perception of the difficulty of the exercise.

The intensity level can also be determined according to the percentage of the heart rate (HR) measured immediately at the end of the exercise or during the exercise relative to the maximum HR. The maximum HR can be calculated, for example, by subtracting the user's age from 220. In this case, the intensity level can be determined after the exercise performance.

To complete the test, the user can perform exercise of a certain level/intensity for a known period of time "T" (e.g. 30 min.<T<2 h.), and after the planned exercise is completed, the BG can be sensed and measured at the end of the tested time, "T".

To enable accurate, quantitative recommendations for achieving exercise related glycemic control, the fundamental pump parameters such as CIR, IS, and basal insulin profile, should be properly assessed and periodically re-evaluated. Also, to improve the accuracy of the results, the patient should avoid additional food intake or insulin delivery modification during the test. In some implementations, the test may not be carried out during stressed condition (illness, menses, etc.) because of increased basal requirements that could alter the accuracy of the tailoring of the exercise-related glycemic control regimen.

As illustrated in FIG. 4, at the end of exercise (i.e. after time "T" has elapsed), the BG may be left unchanged, decreased or increased, based on the change in the user's BG before and after the exercise, and, also, based on the threshold value (e.g. 30 mg/dL). The threshold value may be higher or lower. It may be selected by the user and/or by the medical professional.

In a situation when the difference in BG between the beginning and the end of the exercise is greater than the threshold value (situation II), the desired basal rate can be determined in accordance with the following procedure (according to some embodiments):
 a. The amount of insulin (N) given during the exercise period (T), is N=T*Basal.
 b. The difference in BG between the beginning and the end of the exercise is defined as $\Delta = BG_{beginning} - BG_{end}$.
 c. The desired amount of insulin (N'=T*Basal') to be delivered may be computed as follows:

$$N' = N - (\Delta/IS).$$

d. The desired basal rate (Basal') may therefore be computed as:

$$Basal' = Basal - \frac{\Delta}{IS*T}$$

In general, if the selected physical activity is to be performed in the future, the basal rate can be decreased by:

$$\frac{\Delta}{IS*T}[U/h].$$

If a negative value is obtained when $$\frac{\Delta}{IS*T}$$

is decreased from the basal rate at the time of exercise, it can be recommended to the user to consume carbohydrates of the following magnitude:

$$carb = CIR * \left[ (Basal_{min} * t_{exercise}) + \frac{\Delta}{IS*T} * t_{exercise} - Basal * t_{exercise} \right]$$

and the basal rate can be decreased to minimum, "$Basal_{min}$" (e.g. 0.025 U/h)

If there was RI at the beginning of the test than:

$$Basal' = Basal + \frac{RI}{T} - \frac{\Delta}{IS*T}$$

If the selected physical activity is to be performed in the future, and the RI existed during the test, the basal rate can be decreased by:

$$\frac{\Delta}{IS*T} - \frac{RI}{T}[U/h],$$

wherein the RI refers to the residual insulin during the test.

In a situation when the difference in BG between the beginning and the end of the exercise is smaller than −30 mg/dL (or any other number chosen by the user, caregiver, or physician) (situation III in FIG. 4), the desired basal rate can be determined in accordance with the following procedure according to some embodiments:
 a. The amount of insulin given during the exercise period (T), is N=T*basal.

b. The difference in BG between the beginning and the end of the exercise can be defined as $\Delta = BG_{beginning} - BG_{end}$.

c. The desired amount of insulin (N') to be delivered can be computed as follows:

$$N' = N + (|\Delta|/IS).$$

d. The desired basal rate (Basal') is therefore computed as:

$$Basal' = Basal + \frac{|\Delta|}{IS * T}$$

In general, if the selected physical activity is to be performed in the future, the basal rate can be increased by:

$$\frac{|\Delta|}{IS * T}[U/h].$$

Situation III can be encountered in anaerobic exercise or in competitive sports where a large amount of catecholamines (counterregulatory to insulin) are secreted.

If there was RI at the beginning of the test than:

$$Basal' = Basal + \frac{RI}{T} + \frac{|\Delta|}{IS * T}$$

If the selected physical activity is to be performed in the future and RI was present during the test, the basal rate can be increased by:

$$\frac{RI}{T} + \frac{|\Delta|}{IS * T}[U/h].$$

In some embodiments, if there is residual insulin at the time of exercise initiation in the future, this parameter can also be taken into account and the exercise basal rate (marked as basal' in the above equations) can further be decreased by $RI_{activity}/t_{activity}$.

If a negative basal rate is obtained according to the calculation $$(\text{i.e. } \underline{Basal - (\Delta/(IS * T)) - (RI_{activity}/t_{activity}) < 0}),$$
$$Basal'$$

than the user can be asked to consume carbohydrates according to the calculation:

$$t_{activity} * Basal' - RI_{activity} + (carb/CIR) = 0$$

$$Carb = (RI_{activity} * CIR) - (t_{activity} * Basal' * CIR)$$

The basal rate can be set to 0 U/h.

Alternatively, the basal rate can be set to minimum (e.g. 0.025 U/h) and the user can be asked to consume the following quantity of carbohydrates:

$$t_{activity} * Basal' - RI_{activity} + (carb/CIR) = t_{activity} * Basal_{min}$$

$$Carb = (RI_{activity} * CIR) - (t_{activity} * Basal' * CIR) + (t_{activity} * Basal_{min} * CIR)$$

In some implementations, a different test can be performed for different intensity levels to determine the optimal required decrease in basal rate. In some implementations, the test can be performed for the type of activities and intensity levels typically practiced by the user.

The tailoring of the exercise-related glycemic control regimen, can also be performed by asking the patient to fast for approximately five hours (or for some tested RI time) and rest. Alternatively, fasting may not be required and RI can be taken into account in the evaluation.

Subsequently to the optional fasting period, the first BG measurement can be performed, during which time the BG level can be sensed and measured. The first BG measurement can typically be performed approximately 90 minutes before the planned exercise (e.g., overlapping step1). Given a BG level in the target range (e.g. 70-120 mg/dL), the user may proceed with the test. Otherwise, the patient may administer a correction bolus dose or ingest glucose until target range value can be obtained.

The basal rate can be changed to prevent potential hypoglycemia during, and after, the exercise phase of the test. The change in the basal rate can be performed 90 minutes before exercise (overlapping step 1). The basal rate can be decreased in a non-user specific manner. In some implementations, the basal rate can be decreased as follows: 5% reduction for very light intensity (e.g. levels 9-10 in the Borg scale), 10% reduction for light intensity (e.g. levels 11-12 in the Borg scale), 20% reduction decrease for moderately hard intensity (e.g. levels 13-14 in the Borg scale), 30% reduction for hard intensity (e.g. levels 15-16 in the Borg scale), 40% reduction decrease for very hard intensity (e.g. levels 17-18 in the Borg scale), and 50% reduction decrease for "very, very hard intensity" (e.g. levels 19-20 in the Borg scale). If anaerobic activity is planned, basal rate may not be changed.

The second BG measurement can be performed right before the beginning of the exercise. The activity performance level of intensity and duration can be determined. The user can perform the determined physical activity at the particular level/intensity for a pre-established period of time "T" (e.g. 30 min<T<2 h.). The BG level can again be sensed and measured at the end of the tested time, "T".

In a situation when the difference in BG between the beginning and the end of the exercise is greater than 30 mg/dL (or any other number chosen by the user, caregiver, or physician) (situation II in FIG. 4), the desired basal rate can be determined in accordance with the following procedure:

a. The amount of insulin given during the exercise period (T), is $$N = T * X * basal, \text{ wherein } X = (100 - \% \text{ reduction})/100.$$

b. The difference in BG between the beginning and the end of the exercise is defined as $$\Delta = BG_{beginning} - BG_{end}.$$

c. The desired amount of insulin (N') to be delivered can be determined as follows:

$$N' = N - (\Delta/IS)$$

d. The desired basal rate (Basal') can therefore be computed as:

$$Basal' = Basal * X - \frac{\Delta}{IS * T}$$

In general, if the selected physical activity is to be performed in the future, the basal rate can be decreased by:

$$(\text{Basal} - X * \text{Basal}) - \frac{\Delta}{IS * T}$$

If there was RI at the beginning of the test than:

$$\text{Basal}' = X * \text{Basal} + \frac{RI}{T} - \frac{\Delta}{IS * T}$$

If the selected physical activity is to be performed in the future, and RI existed during the test, the basal rate can be decreased by:

$$(\text{Basal} - X * \text{Basal}) - \frac{\Delta}{IS * T} + \frac{RI}{T} [U/h]$$

In a situation when the difference in BG between the beginning and the end of the exercise is smaller than −30 mg/dL (or any other number chosen by the user, caregiver, or physician) (situation III in FIG. 4), the desired basal rate can be determined in accordance with the following procedure:
 a. The amount of insulin given during the exercise period (T), is =T*X*basal, wherein X=(100−% reduction)/100.
 b. The difference in BG between the beginning and the end of the exercise is defined as Δ=BG$_{beginning}$−BG$_{end}$.
 c. The desired amount of insulin (N') to be delivered can be determined as follows: N'=N+(Δ/IS).
 d. The desired basal rate (Basal') can therefore be computed as:

$$\text{Basal}' = X * \text{Basal} + \frac{|\Delta|}{IS * T}$$

In general, if the selected physical activity is to be performed in the future, the basal rate can be decreased by $$\frac{|\Delta|}{IS * T} + (\text{Basal} - X * \text{Basal}).$$

If there was RI at the beginning of the test than:

$$\text{Basal}' = X * \text{Basal} + \frac{RI}{T} + \frac{|\Delta|}{IS * T}$$

If the selected physical activity is to be performed in the future and RI was present during the test, the basal rate can be decreased by:

$$(\text{Basal} - X * \text{Basal}) + \frac{RI}{T} + \frac{|\Delta|}{IS * T} [U/h]$$

In some embodiments, the basal rate required for exercise is not expressed by Basal rate decrease or increase (U/h) but rather by percentage of basal rate reduction or increment (%). If Basal'<Basal than:

$$\left(1 - \frac{\text{Basal}'}{\text{Basal}}\right) * 100 = \% \text{ Rduction}$$

If Basal'>Basal than:

$$\left(\frac{\text{Basal}'}{\text{Basal}} - 1\right) * 100 = \% \text{ Increment}$$

If the selected physical activity is to be performed in the future, the basal rate can be decreased or increased according to the percent reduction or percent increment.

The user may change the intesity level throughout the physical activity via the user interface. In some embodiments, the user can change the intensity by virtue of pressing buttons/switches or by an audible command. In response to the change of intensity level, the basal rate can also be modified based on a user's approval or automatically.

In some embodiments, upon termination of the physical activity, the basal rate can return to its previous rate. For example, a previous rate can correspond to the basal rate prior to the physical activity, a basal rate pre-programmed by the user, or a new basal rate. The basal rate modification can be carried out automatically or require a confirmation of the user.

In some embodiments, the insulin dispensing device may communicate with adjunctive devices that monitor different parameters of the user's activity, to adjust the tailored regimen for achieving better glycemic control during and/or around exercise time.

During aerobic exercise, the body utilizes more oxygen than at rest. As the exercise intensity increases and more oxygen is needed, the heart rate must increase to meet the demand. One technique to estimate exercise intensity is by measuring exercise heart rate. This can be done using the "Karvonen Formula":

$$CHR=[(MHR-RHR)*\% \text{ Intensity}]+RHR$$

Where CHR—current heart rate (HR reached during exercise), MHR—maximum Hr (220-age), RHR—resting HR The insulin dispensing device can communicate with an electronic heart rate monitor worn by the user. The intensity level can be derived from the heart rate, and the insulin regimen can be adjusted accordingly (as determined during the tests described above). The basal rate may change with or without user interface throughout the practice in accordance with the intensity level mirrored by the changing heart rate. This can be particularly beneficial for users who engage in exercises of varying intensity levels (e.g. basketball game—playing on the court or sitting on the bench) without the need for frequent pump settings.

In some embodiments, the insulin dispensing device can communicate with a foot war (e.g. sneaker) based sensor that can indicate the running or walking pace (particularly in circumstances involving running activities). The measured pace can be translated to intensity levels according to user settings (e.g. 6 mph may be set by the user as light intensity or levels 9-11 in the Borg scale, 9 mph may be set as very hard intensity or 17-18 in the Borg scale).

A communication link between the insulin dispensing device, the heart rate monitor and a sneaker-based sensor can also be established. Such embodiments, in addition to providing a tailored exercise-related insulin regimen, may also serve as a training program for the diabetic runner. The intensity level can be derived from the heart rate and insulin can be delivered accordingly. As the user gets more trained, a lower heart rate can be reached with increasing running (or walking) pace. That is, a certain pace may initially be considered very hard intensity (e.g. 90% maximum HR) but may later become a moderately hard intensity pace (e.g. 70% maximum HR). In such embodiments, the user may be provided with a training log and training recommendations.

The pump may be configured to remind the user to perform a test for determination of a tailored exercise-related basal profile according to intensity level every predetermined period of time (e.g. every 6 months).

Figure 5A:
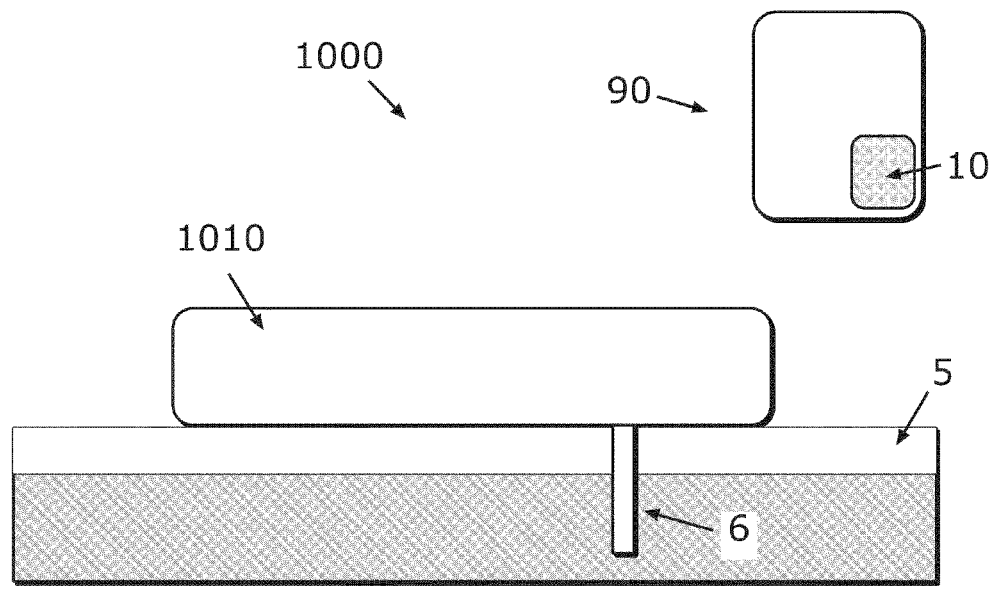
FIGS. 5a-b illustrate embodiments of an exemplary device including an insulin infusion pump unit, a glucose measurement unit, and the exercise glycemic control feature.
Figure 5B:
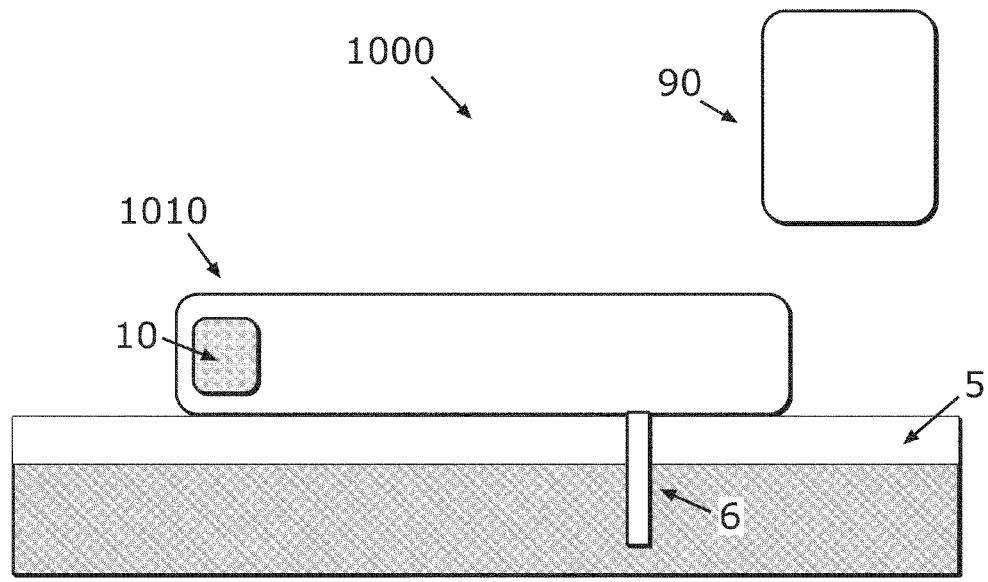

FIGS. 5a-b show embodiments of a device 1000 that can be configured to dispense a therapeutic fluid, e.g., insulin in a patient. The device schematically depicted in both FIGs. can comprise an insulin infusion unit 1010, configured as a pump, a separate glucose measurement unit (e.g. glucometer) 90, and the exercise glycemic control feature 10. In some embodiments, the insulin infusion pump unit 1010 may include a cannula 6 that penetrates the skin 5 to allow delivery of insulin to the patient.

As shown in FIG. 5(a), the exercise glycemic control feature 10 can be located in the glucose measurement unit 90. According to the FIG. 5(b), the exercise glycemic control feature 10 can be located in the insulin infusion pump unit (1010).

In some embodiments (not shown), the insulin infusion pump unit can communicate with a remote control unit allowing programming, user inputs and data acquisition. In some embodiments, the exercise glycemic control feature may be located in the remote control unit.

The glucometer may or may not be a separate item. For example, it can be retrofitted within insulin infusion pump or may be installed in the remote control unit. Other configurations and embodiments of the device, in which the exercise glycemic control feature is located either in the glucometer, or in the pump unit, or in the remote control unit may be implemented and used.

The device may include an insulin infusion pump unit, a continuous glucose measurement (CGM) unit, and the exercise glycemic control feature. In some embodiments, the exercise glycemic control feature may be located in either the pump or the CGM unit.

The insulin infusion pump may comprise a continuous glucose measurement (CGM) unit. The infusion pump unit and continuous glucose measurement (CGM) unit may be located in the same housing and may communicate with a remote control unit. The exercise glycemic control feature may be located either in the CGM or in the pump unit, or in the remote control unit.

Figure 6A:
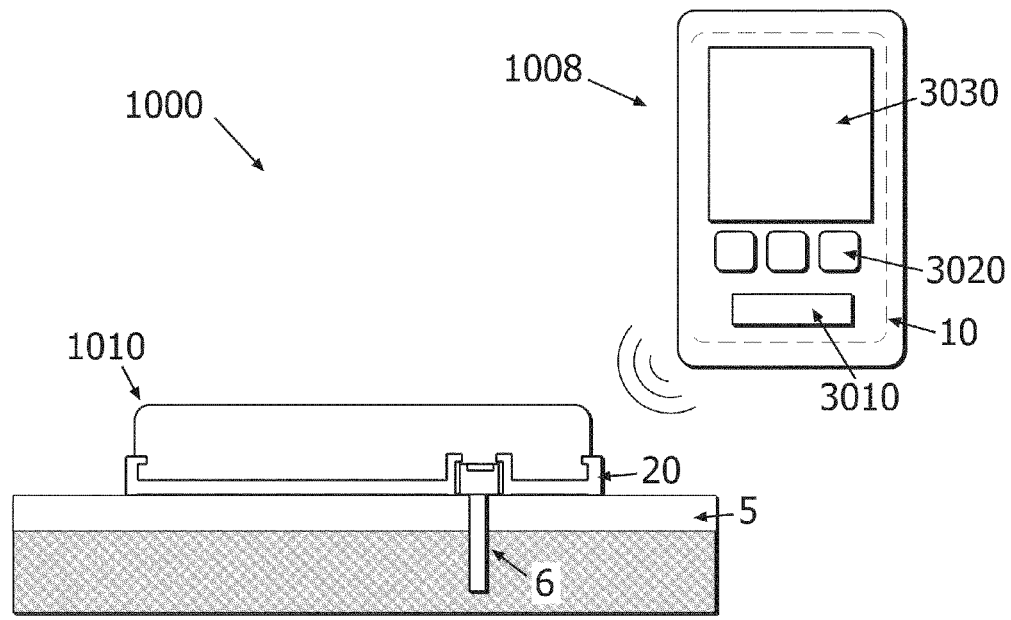
FIGS. 6a-c illustrate embodiments of an exemplary insulin infusion device having an insulin dispensing unit and a remote control unit that contains the exercise glycemic control feature.
Figure 6B:
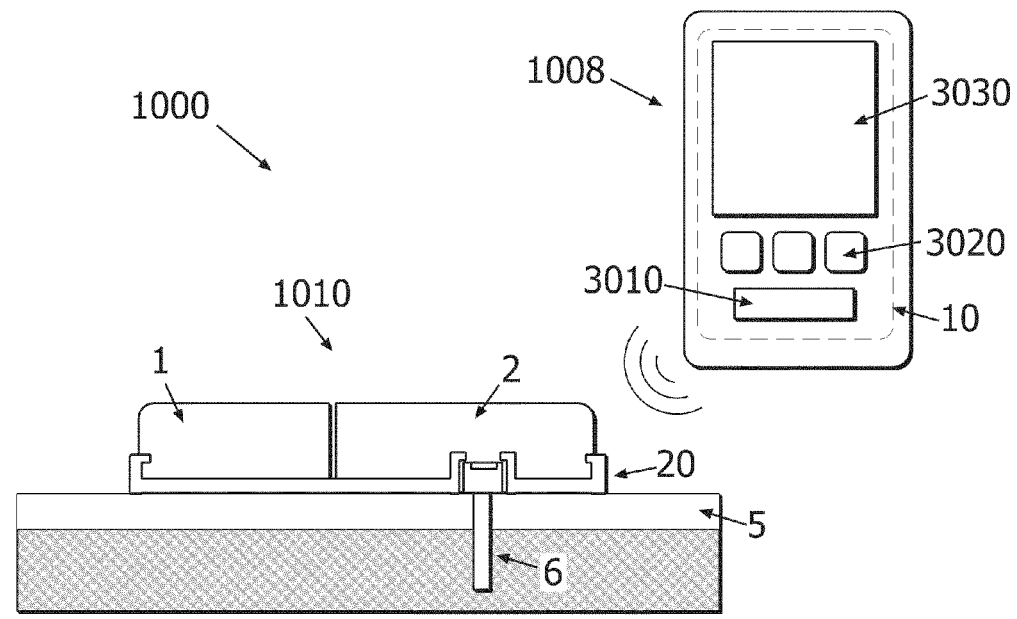
Figure 6C:
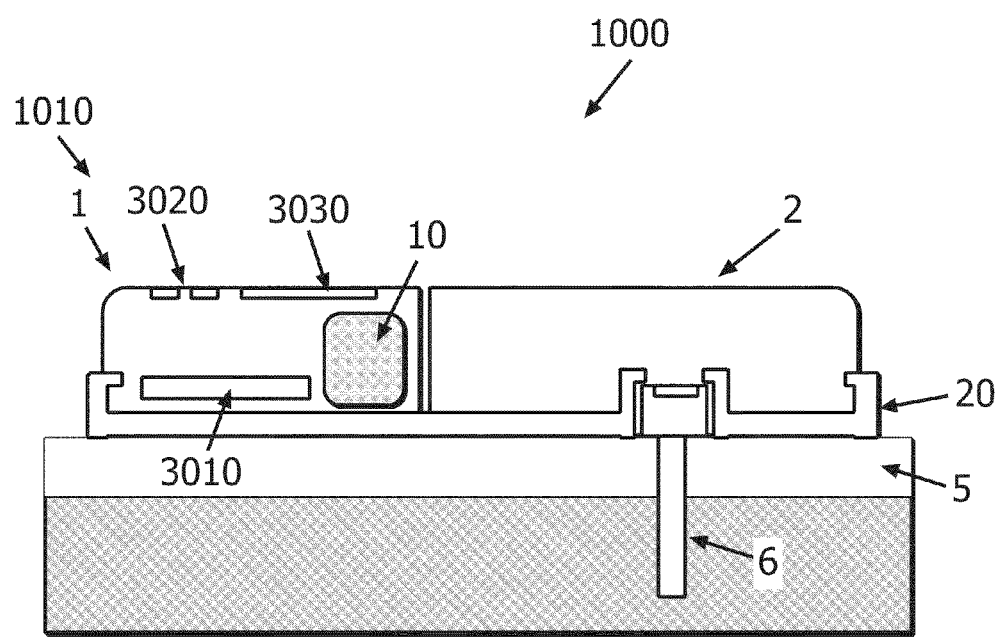

FIGS. 6a-c show embodiments of a device, in which an insulin infusion pump unit 1010 is configured as a patch unit, which can be secured to the user's skin 5. The device can comprise a remote control unit 1008, which can communicate with the patch unit, enabling programming, user inputs and data acquisition.

Manual inputs can be effected by switches/buttons (not shown in FIGS. 6a-b) located on the patch unit. The patch unit can be configured to include one part in one housing as shown in FIG. 6a. Alternatively, the patch unit can be configured to include two parts: a reusable part 1 and a disposable part 2, as shown in FIGS. 6b-c.

In some embodiments, the patch unit can be configured to include a cannula 6 that penetrates the skin 5 to allow delivery of insulin to the patient. The patch unit 1010 can be attached to a dedicated cradle unit 20 that can be a flat sheet adhered to the user's skin 5 and can enable connection/disconnection of the patch unit 1010. An exemplary arrangement is discussed in co-owned, co-pending International Patent Application No. PCT/IL07/001,578 and U.S. patent application Ser. No. 12/004,837 and U.S. Provisional Patent Application No. 60/876,679, the contents of which are hereby incorporated by reference in their entireties.

In some embodiments, as shown in FIGS. 6a-b, the remote control unit 1008 may contain the exercise glycemic control feature 10 which can comprise a processor 3010, an input device 3020 and a display device 3030. The input device may be required for programming the exercise glycemic control feature 10. This input device may be also used for programming the patch unit 1010. The remote control unit 1008 may be configured to include an output (e.g., announcement) device such as a speaker, a vibrating element, or any other suitable device. Alternatively, as shown in FIG. 6c, the exercise glycemic control feature 10 is located in the patch unit 1010.

Figure 7B:
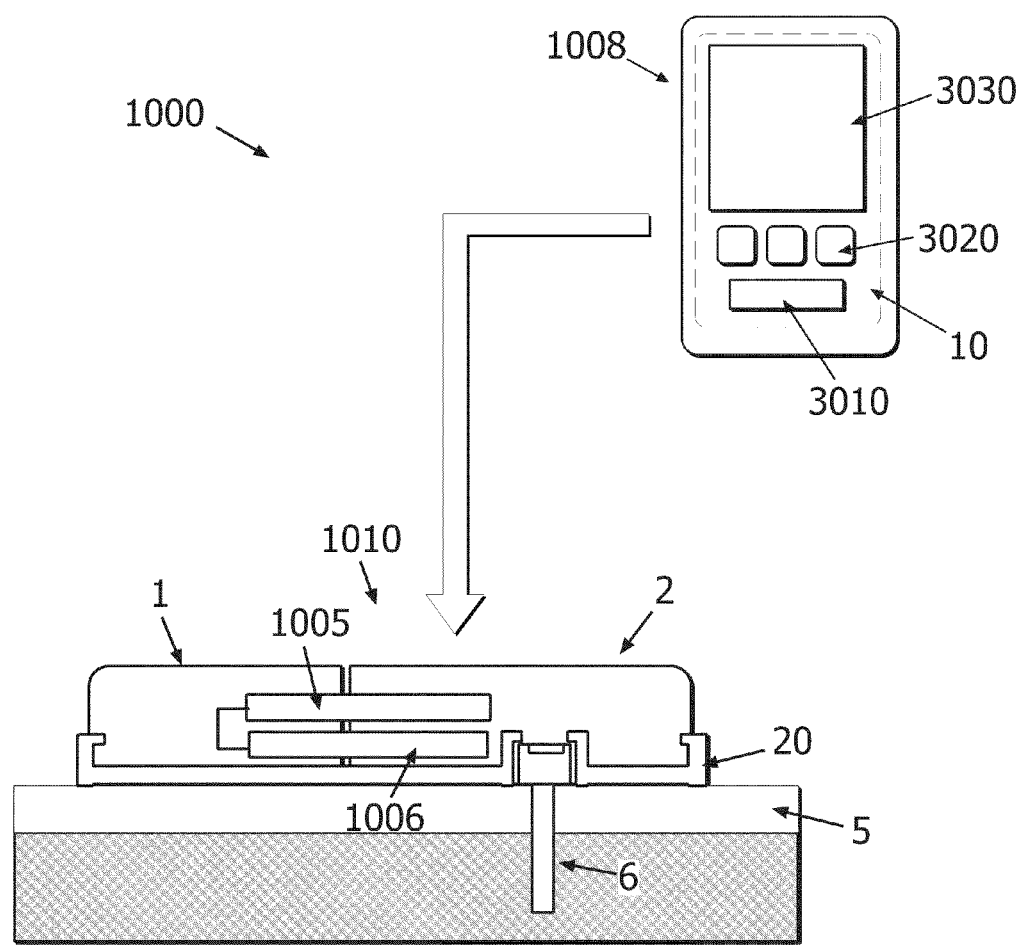

FIGS. 7a-b illustrate embodiments of an exemplary insulin infusion device, wherein the blood glucose readings, required for functioning of the exercise glycemic control feature 10, can be received from a dedicated, continuous subcutaneous glucose monitor 1006. A communication channel between the continuous subcutaneous glucose monitor 1006 and the exercise glycemic control feature 10 residing in the remote control unit 1008 can be maintained, enabling programming, data handling, and user inputs.

FIG. 7a shows the current blood glucose (BG) being measured by an independent continuous subcutaneous glucose monitor 1006. FIG. 7b shows the continuous subcutaneous glucose sensing monitor 1006 being integrated within the patch unit 1010 of the insulin delivery device.

The insulin infusion device can include a dispensing apparatus 1005 and glucose sensing apparatus 1006, which together can constitute a single delivery device. This delivery device may use a single cannula 6 shared by both dispensing and sensing apparatus as described in detail in U.S. application Ser. No. 11/706,606, [U.S. publication 2007-0191702], International Patent Application No. PCT/IL07/001,579 and U.S. patent application Ser. No. 11/963,481, the contents of which are hereby incorporated by reference in their entireties.

Alternatively (not shown), the sensing apparatus and the dispensing apparatus may have separate cannulae that can penetrate the skin 5 and reside in the subcutaneous tissue. The insulin infusion device of this embodiment may be comprised of two parts—a reusable part 1 and a disposable part 2, each part having a corresponding housing. The patch unit 1010 can be attached to a dedicated cradle unit 20 adhered to the user's skin 5. The cradle unit 20 can allow easy connection/disconnection of the patch unit 1010.

FIG. 8 illustrates an exemplary flow chart representing a procedure for testing and tailoring the insulin regimen for an exercise of a particular intensity level. The procedure can include several operations corresponding to a test procedure in which the BG of the patient can be sensed and measured and the adequate basal insulin regimen can be tailored. In some embodiments, the procedure can advise 60 that the user may be required to abstain from food and avoid strenuous physical activity for a specified period of time (e.g., at least 5 hours) prior to the beginning of the test procedure and check the BG level. The patient's blood glucose level ("BGbeginning") can be in the pre-exercise target range (e.g. 80 mg/dL<BG<150 mg/dL). If this condition is not fulfilled, at 61, the user can correct his/her BG by administering a correction bolus (CB) if the BG is too high or by consuming carbohydrates (CC) if the BG is too low.

At 62, the procedure can involve use of three patient parameters: an adequate (resting) basal profile, carbohydrate to insulin ratio (CIR), and insulin sensitivity (IS). At 63, the exercise of a pre-determined intensity and duration (T) can be performed by the patient. The intensity and duration may alternatively be inputted after the exercise performance. The intensity level of the exercise may be determined based upon user subjective conception of the difficulty of the exercise or upon percentage of measured heart rate of the maximum HR. After exercise termination, at 64, the BG level ("BGend") can be sensed and measured.

At 65, the difference between the BG measured at the beginning of the exercise and at the end of the exercise (i.e. Δ=BGbeginning−BGend) can be computed. If the computed difference |Δ|<30, or any other pre-defined threshold value set by the user or someone else (e.g., a physician), at 66, the resting basal rate may be deemed adequate for the tested level of activity.

At 67, if Δ>30, the resting basal rate may be deemed too high for the tested level of activity and can be decreased by Δ/(IS*T) in future exercises of similar levels of intensity. If a negative value is obtained when $$\frac{\Delta}{IS*T}$$

is decreased from the basal rate at the time of exercise (not shown) then the user may be advised to consume carbohydrates of the following recommended magnitude:

$$carb = CIR * \begin{bmatrix} (Basal_{min} * t_{exercise}) + \\ \frac{\Delta}{IS*T} * t_{exercise} - \\ Basal * t_{exercise} \end{bmatrix}$$

Under these circumstances, the user's basal rate would thus be decreased to the minimum value ("Basalmin"). At 68, if Δ<−30, the resting basal rate is too low for the tested level of activity and may be increased by |Δ|/(IS*T) in future exercises of similar levels of intensity. This scenario is less likely to occur but might happen in anaerobic type of activities.

In some embodiments, the tests can be performed for different levels of exercise intensity. When the user performs an exercise in the future, he/she may be asked to input the intensity level of the exercise and whether the exercise is aerobic or aneaorobic. The adequate basal rate may then be set according to the performed tests.

In some embodiments (not shown), the user may not be required to fast and the residual insulin of the bolus given to counteract the carbohydrates consumed in the meal prior to exercise is taken into account in the course of performing the procedure depicted in FIG. 8.

If the selected physical activity is to be performed in the future, and RI existed during the test, the basal rate can be decreased by:

$$\frac{\Delta}{IS*T} - \frac{RI}{T} [U/h]$$

for Δ>30 or increased by:

$$\frac{RI}{T} + \frac{|\Delta|}{IS*T} [U/h]$$

for Δ<−30

In some embodiments, if there is residual insulin at the time of exercise initiation in the future (i.e. RIactivity), the exercise basal rate (Basal') is further decreased by RIactivity/tactivity. If a negative basal rate is obtained (i.e. Basa'−(RIactivity/tactivity)<0), then the user may be advised to consume carbohydrates according to the following calculation:

$$Carb = (RI_{activity} * CIR) - (t_{activity} * Basal' * CIR)$$

The basal rate would be set to 0 U/h.

Alternatively, the basal rate can be set to minimum (e.g. 0.025 U/h) and the user may be asked to consume the following amount of carbohydrates:

$$Carb = (RI_{activity} * CIR) - (t_{activity} * Basal' * CIR) + (t_{activity} * Basal_{min} * CIR)$$

In some embodiments, a continuous glucose monitoring unit ("CGM") may be used in conjunction with the insulin regimen feature. In such embodiments, glucose measurements are continuously carried out by the CGM unit. The CGM unit may alarm the patient when the CBG drops rapidly or is too low during the test.

Figure 9:
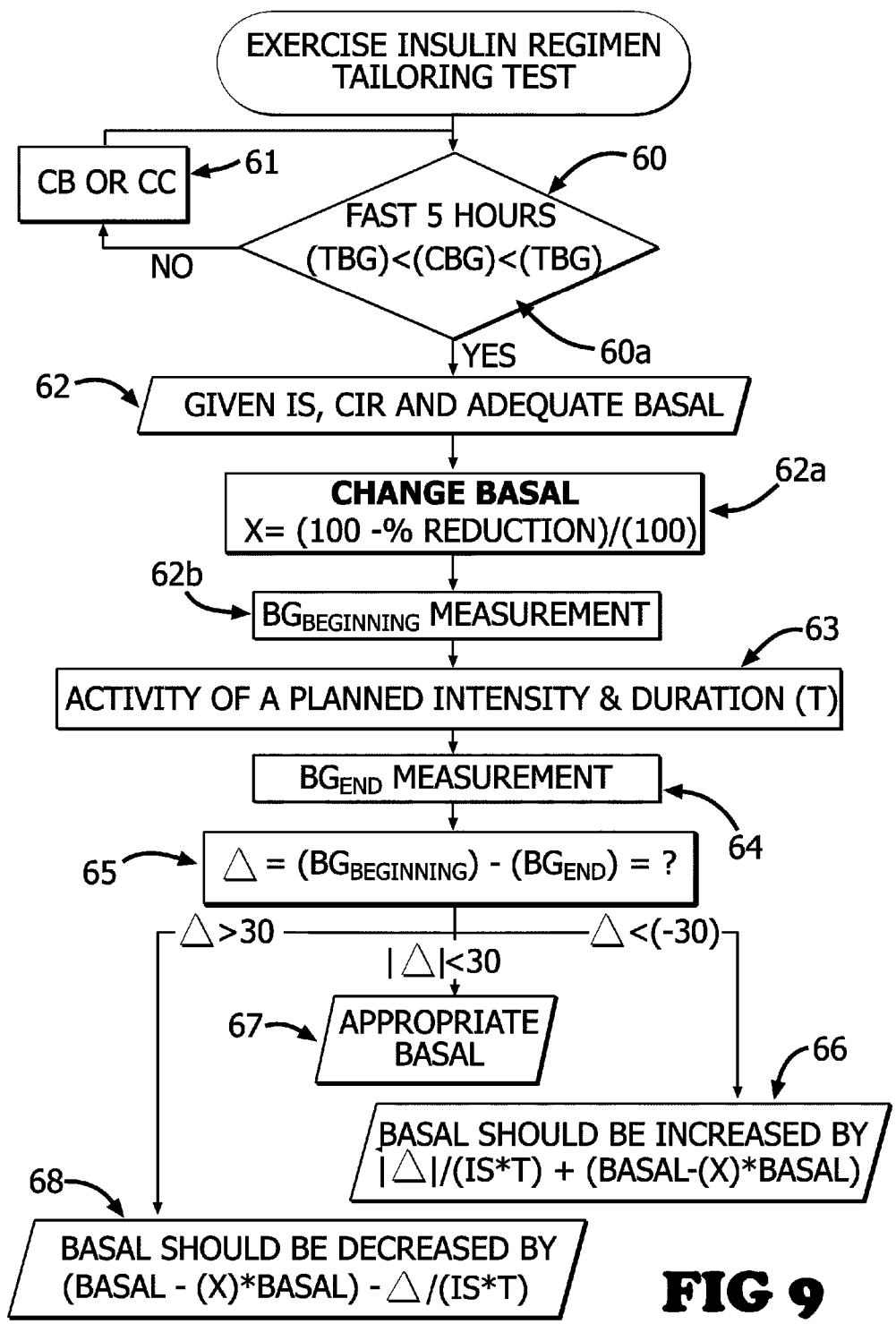
FIG. 9 is an exemplary block diagram representing another algorithm of the exercise glycemic control feature.

FIG. 9 illustrates an exemplary flow chart representing another procedure for testing and tailoring the insulin regimen for an exercise of a certain level of intensity. The depicted procedure can be implemented in the exercise-related insulin regimen feature.

For example, according to FIG. 9, at 60, the user may be advised that he/she is required to fast prior to the beginning of the test procedure and have the user's current BG level determined. The user's blood glucose level ("CBG") can be in the resting target range (e.g. 80 mg/dL<BG<120 mg/dL), as shown by arrow (60a). If this condition is not met, the user corrects 61 his/her BG by administering a correction bolus (CB) if the BG is too high or by consuming carbohydrates (CC) if the BG is too low.

Given an adequate (resting) basal profile, CIR and IS, as indicated 62, the basal rate can be reduced, at 62a, to prevent potential hypoglycemia during and after the performance 63 of the exercise phase of the test. The basal rate reduction operation 62a, can be performed approximately 90 minutes before commencement of the exercise (possibly overlapping operation 60). The pre-test basal rate reduction can adjust the basal rate of the user in a non-user specific manner (i.e. with no correspondence to the user's specific parameters such as IS). As a result, this pre-test adjustment may not be accurate. The basal rate can further be refined to a more accurate value by using the user's specific parameters.

In some embodiments, the basal rate may be decreased according to the following: 10% reduction for light intensity exercise (e.g. levels 9-11 in the Borg scale), 20% reduction decrease for moderately hard intensity exercise (e.g. levels 12-13 in the Borg scale), 30% reduction for hard intensity exercise (e.g. levels 15-16 in the Borg scale), 40% reduction decrease for very hard intensity exercise (e.g. levels 17-18 in the Borg scale), and 50% reduction decrease for a "very very hard" intensity exercise (e.g. levels 19-20 in the Borg scale). If anaerobic activity is planned, basal rate may not be changed.

Before commencement of the exercise operation 63, and approximately 90 minutes after basal rate reduction 62a, the user's BG can be sensed and measured 62b ("BGbeginning"). The procedure then commences the exercise 63, whereupon the user performs an exercise of a pre-determined intensity level and duration (T). The intensity and duration may alternatively be inputted after the exercise performance. At the conclusion of the exercise, the BG level ("BGend") can be sensed and measured 64.

At 65, the difference between the BG measured at the beginning of the exercise and at the end of the exercise (i.e. Δ=BGbeginning−BGend) can be calculated. For example, if

|Δ|<30, or any other pre-defined threshold value set, for example, by the user or physician, the arbitrarily reduced basal rate is determined 67 to be adequate for the tested level of activity. If Δ>30 (or any other pre-defined threshold value set by the user or physician), the resting basal rate deemed to be too high for the tested level of activity and can be decreased 68 for future exercises of similar levels of intensity by:

$$(basal - X*BasaL) - \Delta/(IS*T), \text{ where } X=(100-\% \text{ reduction})/100.$$

If Δ<−30 (or any other number set by the user or physician), the resting basal rate is deemed to be too low for the tested level of activity and can be decreased 66 for future exercises of similar levels of intensity by $$(basal - X*BasaL) + |\Delta|/(IS*T)$$

In some embodiments (not shown), the user may not be required to fast and the residual insulin of the bolus given to counteract the carbohydrates consumed in the meal prior to exercise is taken into account by the procedure depicted in FIG. 9.

Figure 10A:
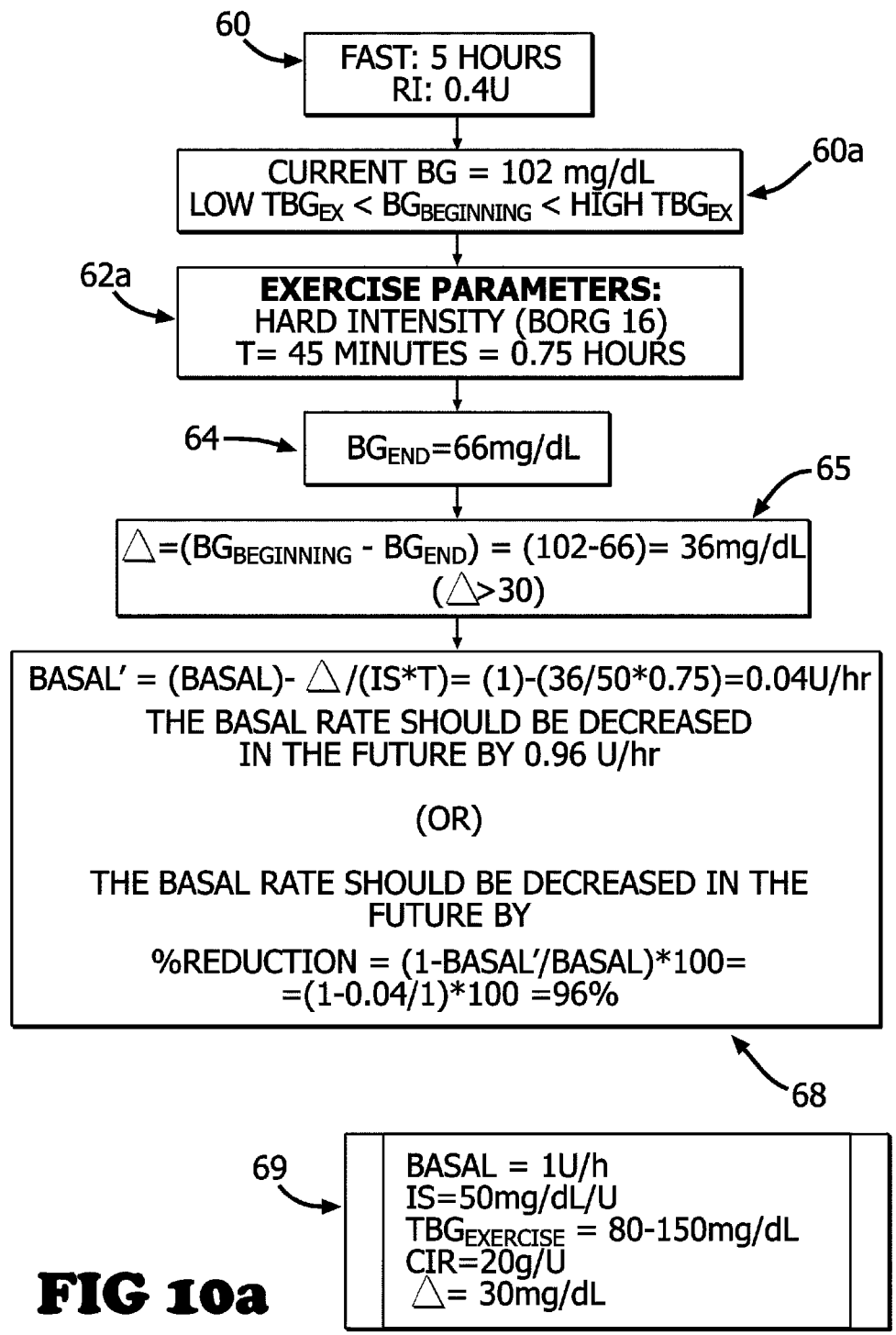
FIGS. 10a-b provide an exemplary algorithm and a user interface for the exercise glycemic control feature.
Figure 10B:
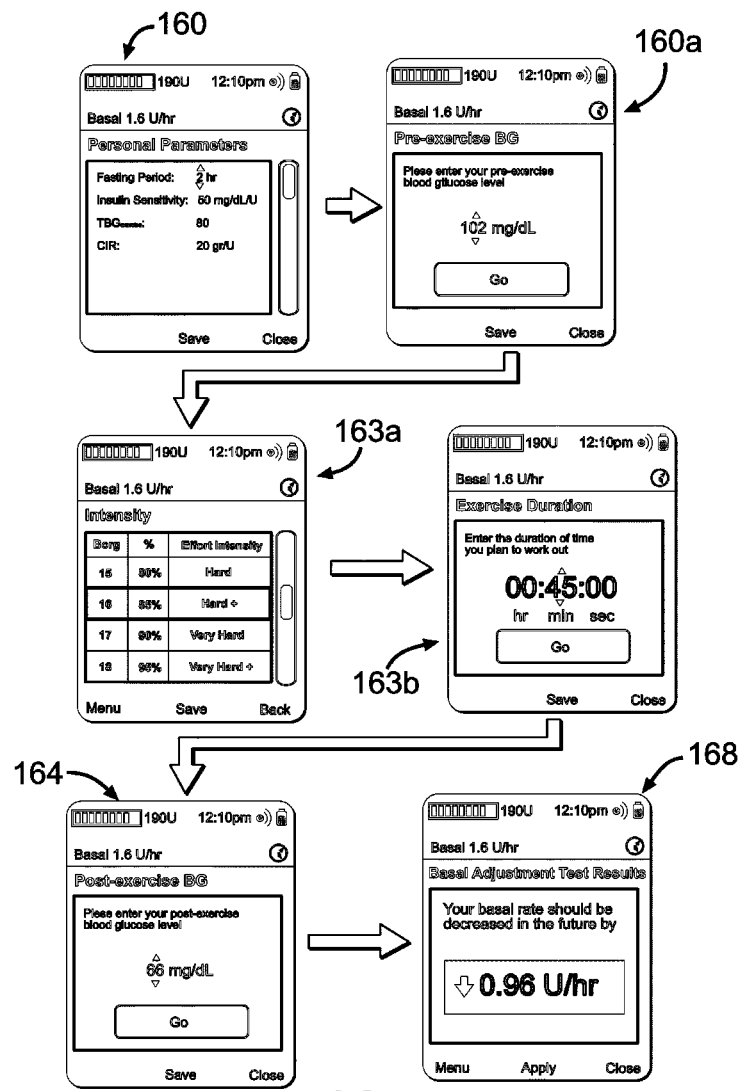

FIGS. 10a-b illustrate an exemplary procedure and a user interface for tailoring exercise-related insulin regimen. As shown in FIG. 10a, the various corresponding parameters 69 can be set as IS=50 mg/dL/U, exercise TBG can be in the range of 80-150 mg/dL, a threshold delta of 30 mg/dL, and the basal rate during the test is 1 U/h.

Under these circumstances, the following operations can be performed. At 60, the patient can be advised that he/she can fast for 5 hours (to eliminate the RI effect). Prior to commencement of an exercise test, the current glucose can be measured at 60a (BG beginning). BG beginning in the example equals 102 mg/dL, which falls in the exercise target zone. The user exercises in a hard intensity level for 45 minutes, as indicated at 62a. The BG can be measured 64 immediately after the exercise, $BG_{end}$=66 mg/dL. The difference between $BG_{beginning}$ and $BG_{end}$ is computed 65, and is determined to be 36 mg/dL in the given example. The basal rate is determined 68 to be decreased by 0.96 U/h if an exercise of a similar intensity is to be performed in the future. Alternatively, the basal rate can be decreased by 96% if an exercise of a similar intensity is to be performed in the future.

FIG. 10b shows one example of a user interface that can be used for exercise glycemic control feature configuration. Panel 160 shows the initial setting of the user's personal parameters needed for the feature. Panel 160a shows the UI of the initial BG measurement (i.e. BGbeginning) required for the test. Panels 163a and b show the UI of the determination of the intensity level, and duration of the exercise of the test. Panel 164 shows the UI of the BG measurement after the exercise (i.e. BGend) required for the test. Panel 168 shows the UI of the test result, i.e. the basal insulin regimen required for future exercise of similar intensity level.

Figure 11:
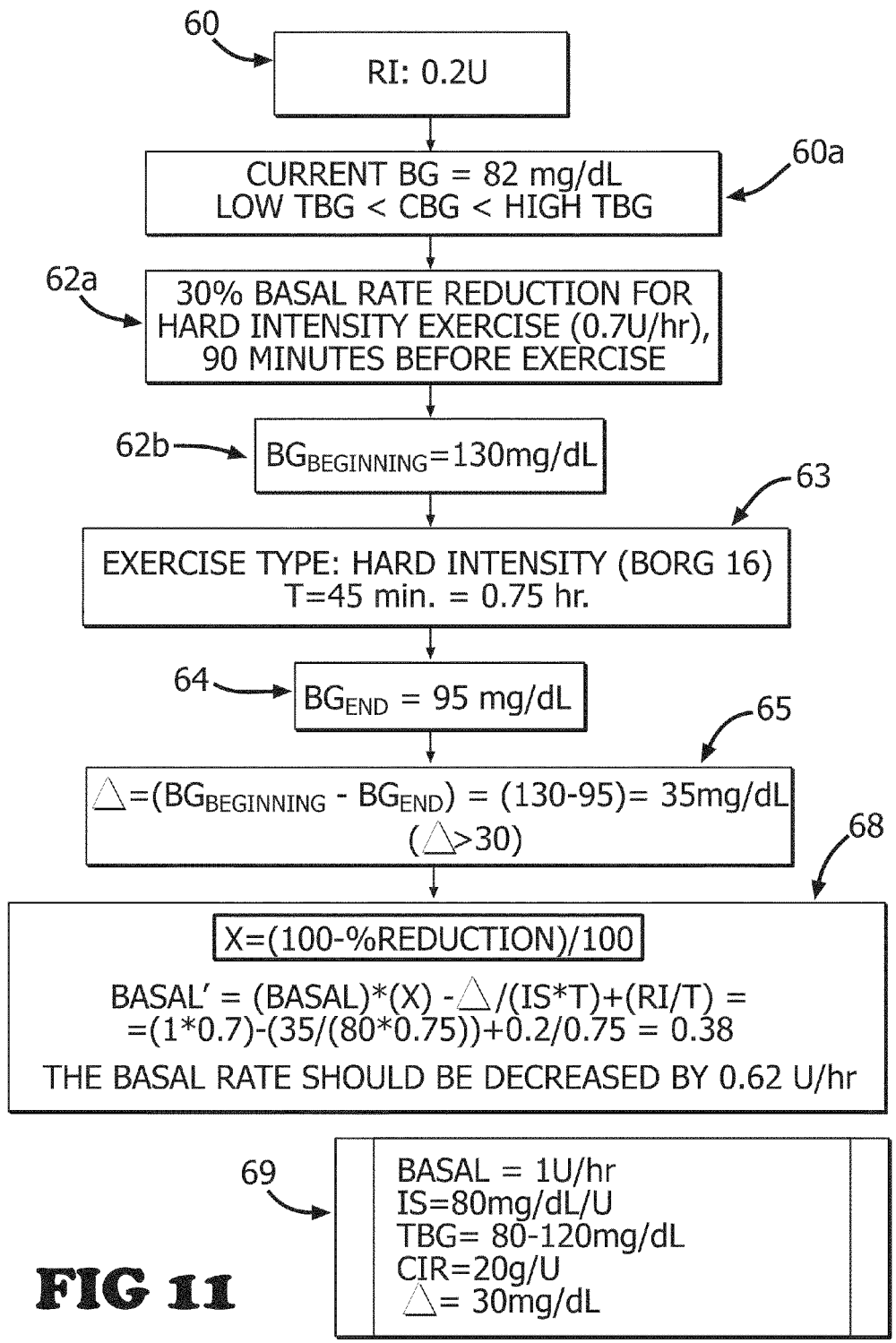
FIG. 11 provides another exemplary algorithm for the exercise glycemic control feature.

FIG. 11 illustrates exemplary operations, corresponding to a portion of the procedure described in relation to FIG. 9. Specifically, FIG. 11 illustrates a particular example of testing and tailoring the insulin regimen for an exercise of a certain intensity. As shown, the various corresponding parameters 69 are set as IS=80 mg/dL/U, TBG is in the range of 80-120 mg/dL, a threshold delta of 30 mg/dL, and the basal rate during the test is 1 U/h.

Given the initial parameters at 69, the patient's residual insulin can be determined at 60 to be 0.2 U based on the magnitude of previous boluses and the time elapsed since the boluses. The current glucose level can be measured 60a. CBG in the example equals 82 mg/dL, which falls in the target zone. The patient can plan an exercise of hard intensity. The basal rate can thus be decreased in a non-user specific manner 62a by 30% (to 0.7 U/h), 90 minutes before exercise commencement.

At 62b, the BG level can be measured immediately before exercise and can be determined to be BGbeginning=130 mg/dL. At 63, the user can exercise at a hard intensity level for 45 minutes. At 64, the BG level can be measured immediately after completion of the exercise and the BG level can be determined to be BGend=95 mg/dL. At 65, the difference between BGbeginning and BGend can be computed, and, according to the given example is determined to be 35 mg/dL. At 68, the determination can be made that the basal rate can be decreased by 0.62 U/h for future exercises of a similar intensity.

FIG. 12 illustrates exemplary operations, corresponding to a portion of the procedure described in relation to FIG. 9. Specifically, FIG. 12 illustrates a particular example for testing and tailoring the insulin regimen for an exercise of a certain intensity. At 69, the initial parameters can be selected as follows: IS=80 mg/dL/U, TBG is in the range of 80-120 mg/dL, a threshold delta of 10 mg/dL, and the basal rate during the test is 1 U/h. In this example, the basal regimen can be expressed in "% Reduction" rather than absolute basal rate reduction (U/h).

Based on the initial parameters identified at 69 as illustrated in FIG. 12, at 60 the patient can be advised that he/she can fast for 5 hours (e.g. to eliminate the effect of RI). At 60a, the current glucose level (CBG) can be measured. For the purposes of this example, CBG equals 140 mg/dL, which does not fall in the target zone. Accordingly, at 61, a correction bolus can be administered. For example, the correction bolus can be selected according to the equation:

$$(CBG-TBG)/IS = (140-100)/80 = 0.5 \text{ U}$$

At 62a, an exercise having a "very hard" intensity level can be planned for the patient. The basal rate can be decreased in a non-user specific manner by 40% (to 0.6 U/h), 90 minutes before exercise initiation. At 62b, the BG level can be measured immediately before commencement of the exercise. In this particular example, the BG level can be determined to be BGbeginning=100 mg/dL. At 63, the user can perform the planned exercise for a period of 30 minutes. At 64, the BG level can be measured immediately after completion of the exercise and the BG level can be determined to be BGend=112 mg/dL. At 65, the difference between BGbeginning and BGend can be determined to be equal to −12 mg/dL, which has an absolute value larger than the Δ of the example. Accordingly, the basal rate can be decreased by 10% for future exercises of similar intensity.

FIGS. 13a-d illustrate a system that can include an insulin dispensing device that can communicate with an electronic heart rate monitor. The patch unit of the insulin dispensing device 1010 can be secured to the user's body. The heart rate monitor 250 can be attached to a belt 252 which can be strapped around the user's chest. The exercise intensity can be estimated according to the sensed heart rate. For example, this can be done using the "Karvonen Formula":

$$CHR = [(MHR-RHR)*\% \text{ Intensity}] + RHR$$

Where CHR—current heart rate (HR reached during exercise), MHR—maximum Hr (220-age), RHR—resting HR The insulin regimen can be adjusted according to the intensity level derived from the continuously sensed HR and according to the basal rate required for each intensity level as tailored to the user by performing the procedures described, for example, in FIGS. 8-9.

Alternatively, the insulin regimen can be adjusted according to the HR derived intensity level and the basal rate required for each intensity level can be adjusted according to general guidelines. For example, the basal rate can be decreased by 10% for light intensity exercises according to the Borg scale. Similarly, the basal rate can be decreased by 20% for moderately hard intensity exercise (e.g. levels 12-13 in the Borg scale), by 30% for hard intensity (e.g. levels 15-16 in the Borg scale), by 40% for very hard intensity (e.g. levels 17-18 in the Borg scale), and by 50% for "very very hard" intensity (e.g. levels 19-20 in the Borg scale).

In some implementations, the basal rate can change with or without user input (provided, for example, through a user interface) throughout the performance of the physical exercise in accordance with the intensity level mirrored by the changing heart rate.

In some embodiments, the pump 1010 can communicate with a display watch 260 which may provide the user with graphical and/or non-graphical data such as the HR, and basal insulin delivery throughout practice and/or around it. If the insulin pump comprises a CGM, then the user's BG can also be displayed.

In some embodiments, earphones 254 may be connected to the insulin pump 1010 so that the user can be audibly notified whenever there is a significant change in HR and/or the basal insulin delivery. If the insulin pump comprises a CGM, any significant change in BG may also be announced.

In some embodiments, the user can set a training program in the insulin pump. For example, the user can set a schedule in which every week, a 10% increase in the working heart rate (compared to maximum HR) can be required. The user can be instructed via the earphones and/or the display watch to decrease or increase intensity level in order to meet the goals of the set schedule. The basal insulin can be delivered according to the selected intensity level.

Figure 13A:
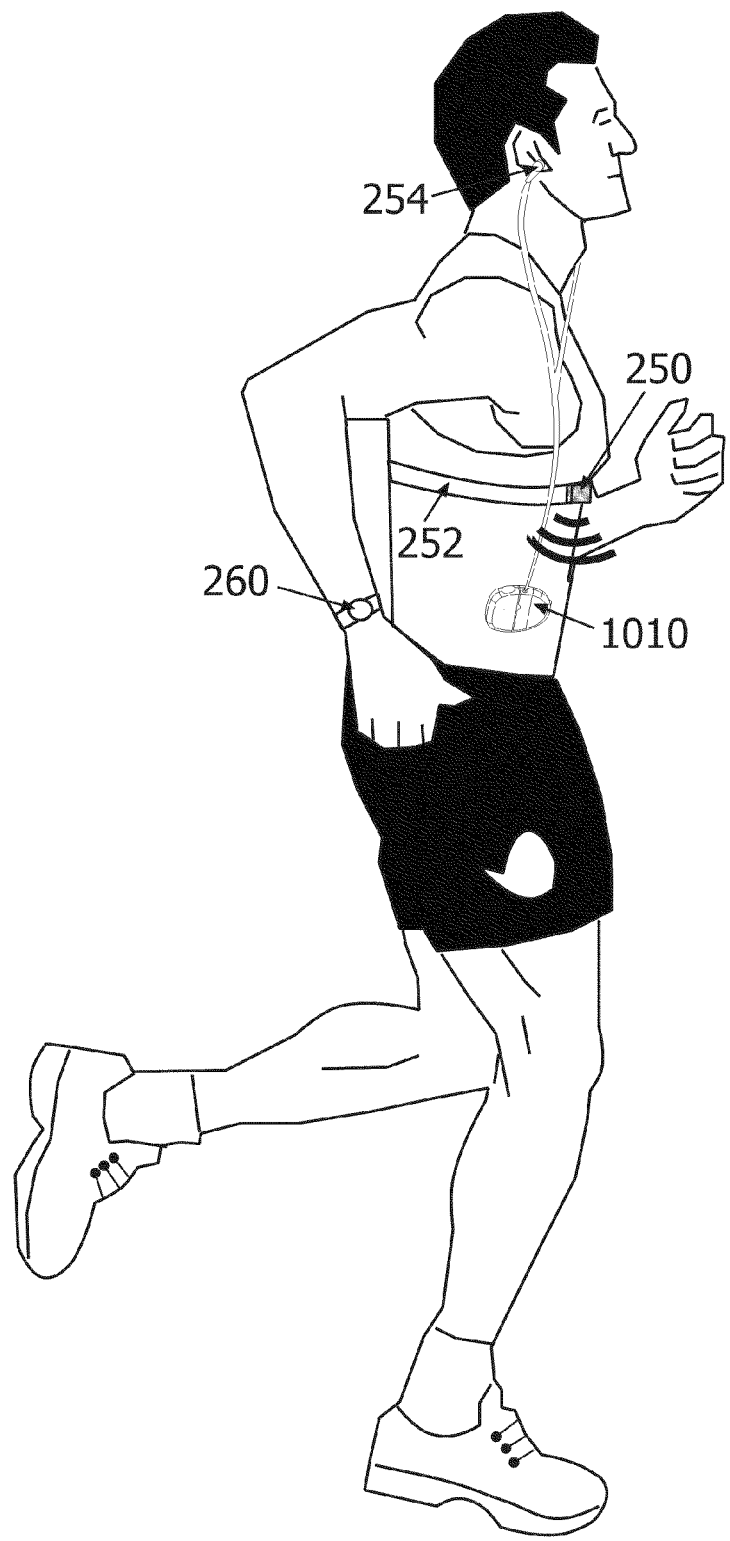
FIGS. 13a-d illustrate an insulin dispensing device that can communicate with an electronic heart rate monitor.
Figure 13B:
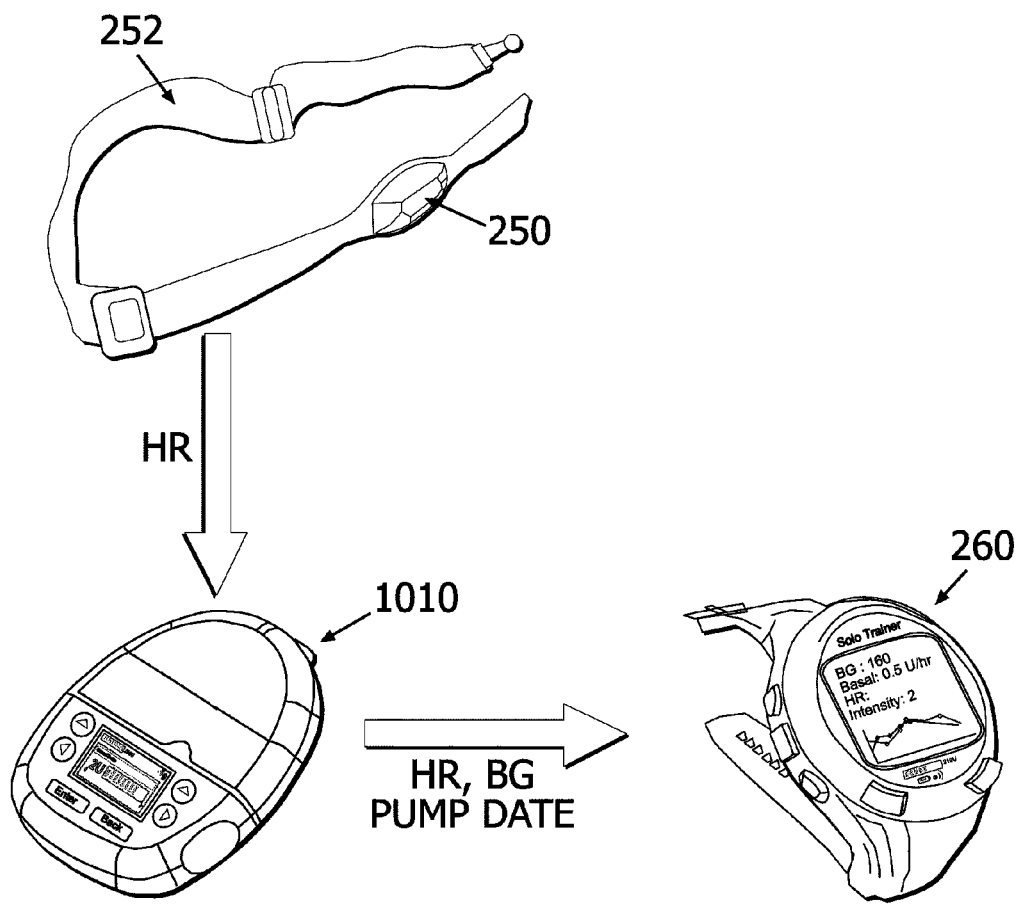
Figure 13C:
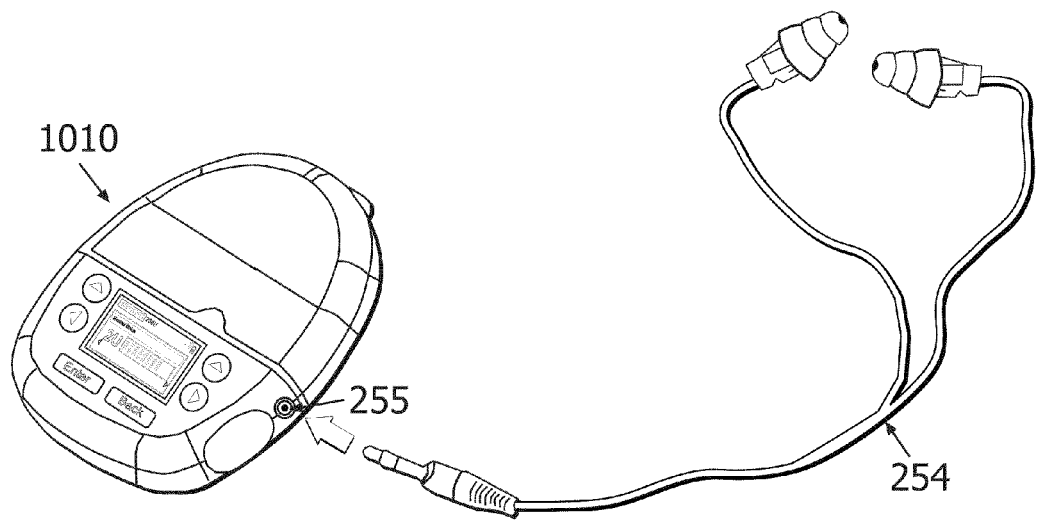
Figure 13D:
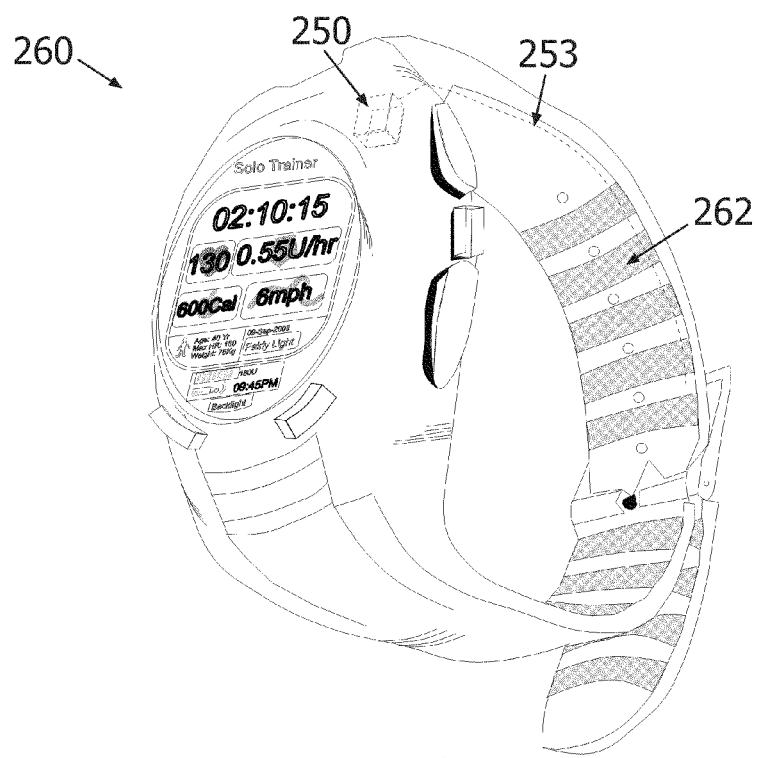

FIG. 13a shows a user with the skin secured patch unit of the insulin dispensing device 1010, the HR monitor 250 strapped around the chest 252, a watch display 260, and earphones 254. FIG. 13b provides a more detailed view of the HR monitor 250, the patch unit of the insulin dispensing device 1010, and the display watch 260. FIG. 13c shows the connection of the earphones 254 to the unit of the insulin dispensing device 1010 via a dedicated outlet port 255 in the patch unit. FIG. 13d shows an exemplary illustration in which the HR monitor 250 is part of the display watch 260. The sensing component of the HR monitor can include electrodes 262 attached to the watch strap, allowing flexibility of the strap, and wiring 253 that connects the different electrodes 262 and the HR monitor itself 250.

Figure 14A:
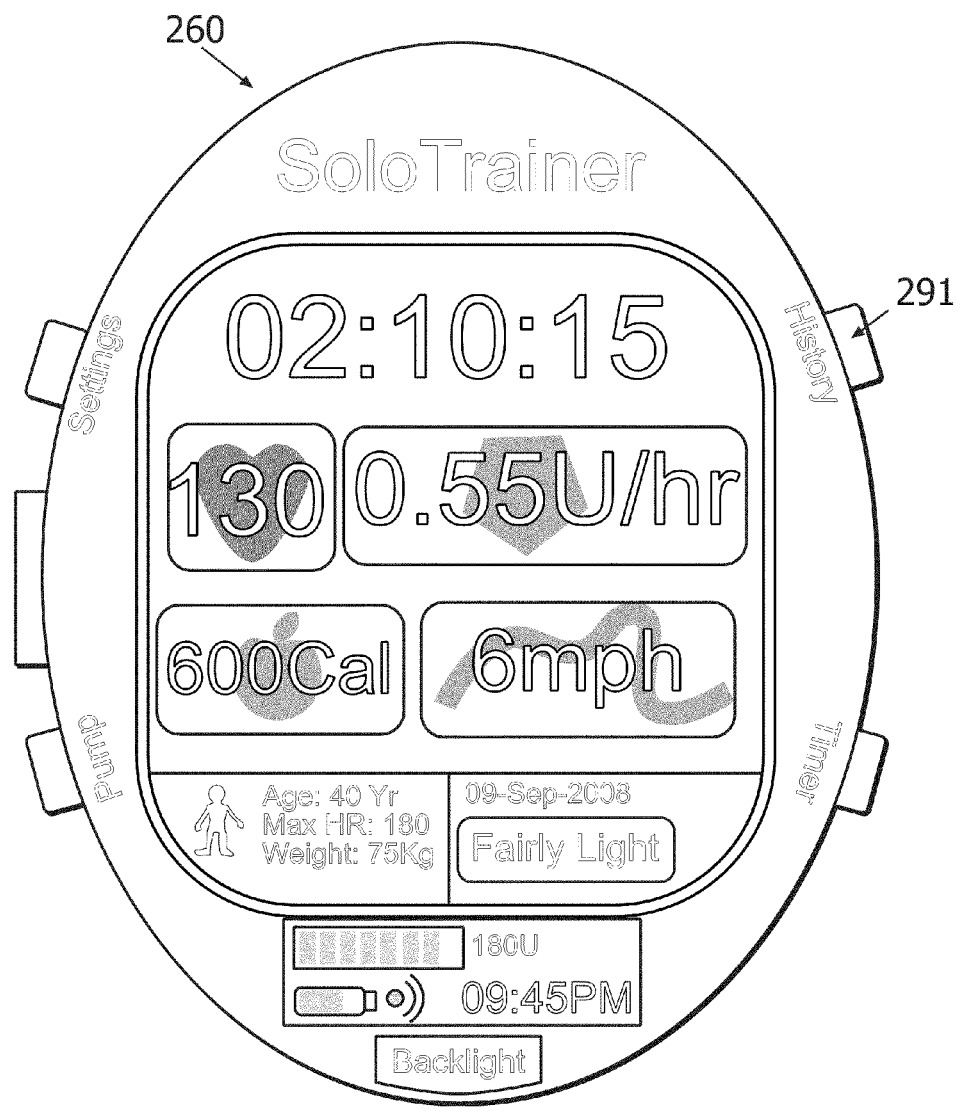
FIGS. 14a-b illustrate an example of a user interface for displaying exercise log data.
Figure 14B:
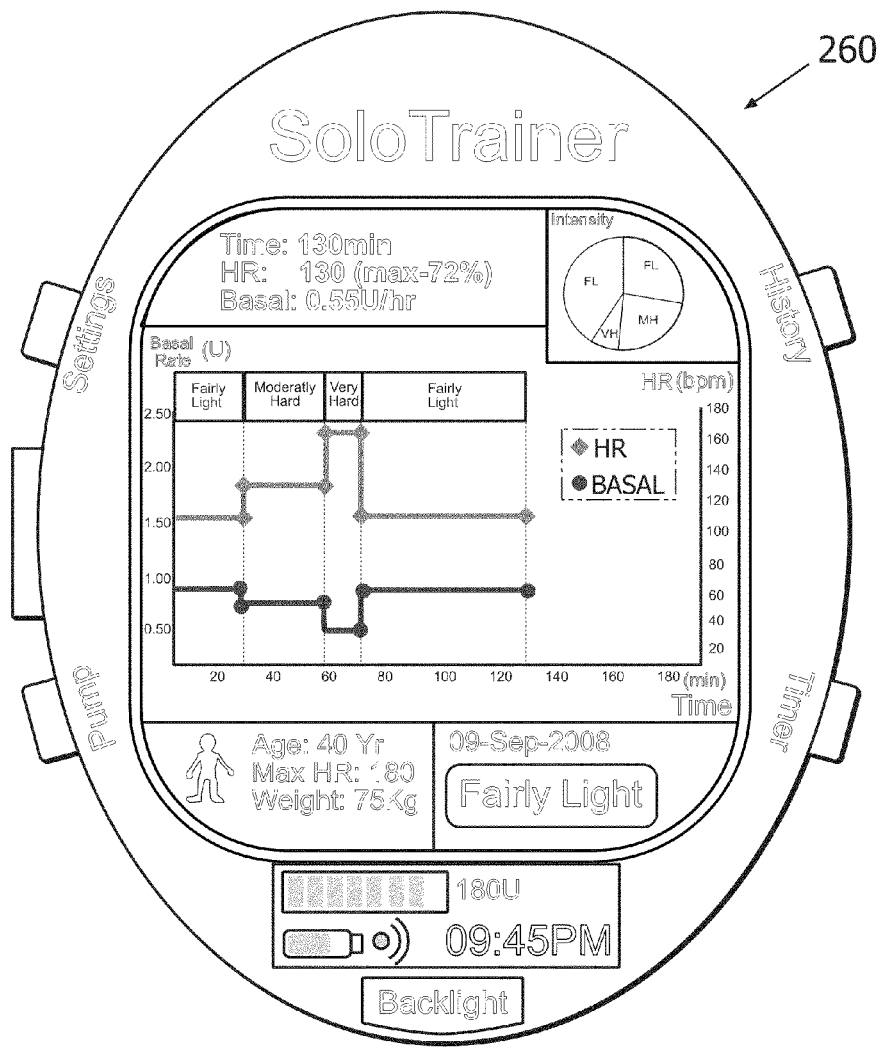

FIGS. 14a-b illustrate examples of a user's exercise log data shown on a display watch 260. As shown, the display watch 260 can communicate with and display data received from the insulin dispensing device that communicates with the HR monitor. Alternatively, the display watch 260 can communicate with the HR monitor directly.

For example, FIG. 14a provides an example of a main menu that can be displayed to the user on a display watch 260. The displayed data can comprise the user's current HR (130 in the example shown), calories burned (600 calories), exercise time (2:10:15 h), intensity level (Fairly light), approximate running pace (6 miles per hour) (this parameter may be derived directly from the HR monitor or from an additional sneaker based sensor), basal rate (0.55 U/h) are displayed. In addition, the displayed data can comprise the battery status, the amount of insulin left in the pump's reservoir, the time and date, and the user's parameters (max HR, age, weight). If the user wishes to view the history of the current exercise, the "history" button 291 can be pressed and the submenu depicted in FIG. 14b can be displayed.

In some embodiment, the "history" submenu can display several graphs: HR vs. time, basal rate vs. time and intensity level vs. time (pie graph). Thus, as shown, the exemplary data displayed on the display watch 260 can indicate that the corresponding user of the example is 40 years old, and that the user has a maximum heart rate of 180 beats/min (maximum HR=220-age). As further indicated in the displayed data, the corresponding user has been exercising for the last 130 minutes and the following readings were received from the HR monitor:

0-32 min: 108-120 beats/min or 60-70% maximum HR;
32-61 min: 126-144 beats/min or 70-80% maximum HR;
61-75 min.: 162-180 beats/min or 90-100% maximum HR;
75 min-now (130 min): 90-108 beats/min or 50-60% maximum HR.

According to the Borg scale:
60-70% maximum HR is considered "fairly light" intensity (Borg 11-12);
70-80% maximum HR is considered "moderately hard" intensity (Borg 13-14);
90-100% maximum HR is considered "very hard" intensity (Borg 18-19);
50-60% maximum HR is considered "very light" intensity (Borg 9-10).

According to the tests performed by the user to tailor the required basal insulin to different levels of intensity (which may have been achieved by performing the procedures depicted, for example, in FIGS. 8 and 9):

"Fairly light" intensity (Borg 11-12) required a reduction of 0.08 U/h, so 0.92 U/h were delivered;
"Moderately hard" intensity (Borg 13-14) required a reduction of 0.25 U/h, so 0.75 U/h were delivered;
"Very hard" intensity (Borg 18-19) required a reduction of 0.45 U/h, so 0.55 U/h were delivered;
"Very light" intensity (Borg 9-10) required a reduction of 0.03 U/h, so 0.97 U/h were delivered.

FIGS. 15 a-b depict a system that includes an insulin dispensing device that can communicate with a sneaker-based sensor. In some embodiments, a sneaker-based sensor 270 (typically used by runners) can indicate the running or walking pace and transmit it to the patch unit of the insulin dispensing device 1010. The pace can be translated to intensity levels, for example, according to user settings (e.g. 6 mph may be set by the user as light intensity or levels 9-11 in the Borg scale, 9 mph may be set as very hard intensity or 17-18 in the Borg scale, etc.). The basal rate can subsequently be regulated according to the intensity level that matches the sensed pace. The basal rate can be changed with or without user input (provided, for example, through a user interface) throughout the physical exercise in accordance with the intensity level mirrored by the changing pace.

In some embodiments, the pump 1010 may communicate with a display watch 260 which may provide the user with graphical and/or non-graphical data regarding the exercise (e.g. pace, distance run, calories burned) and pump parameters (e.g. basal insulin rate, BG).

In some embodiments, earphones 254 may be connected to the insulin pump 1010 and the user can be audibly notified regarding the exercise (e.g. pace, distance run, calories burned) and pump parameters (e.g. basal insulin rate, BG).

In some embodiments, the user can set a training program in the insulin pump. For example, the user can set a schedule in which every week, an additional mile is to be run at a 0.5 mph increase in pace. The user can be instructed via the earphones and/or the display watch to decrease or increase the pace to meet the goals of the set schedule. The basal insulin can be delivered accordingly.

Figure 15A:
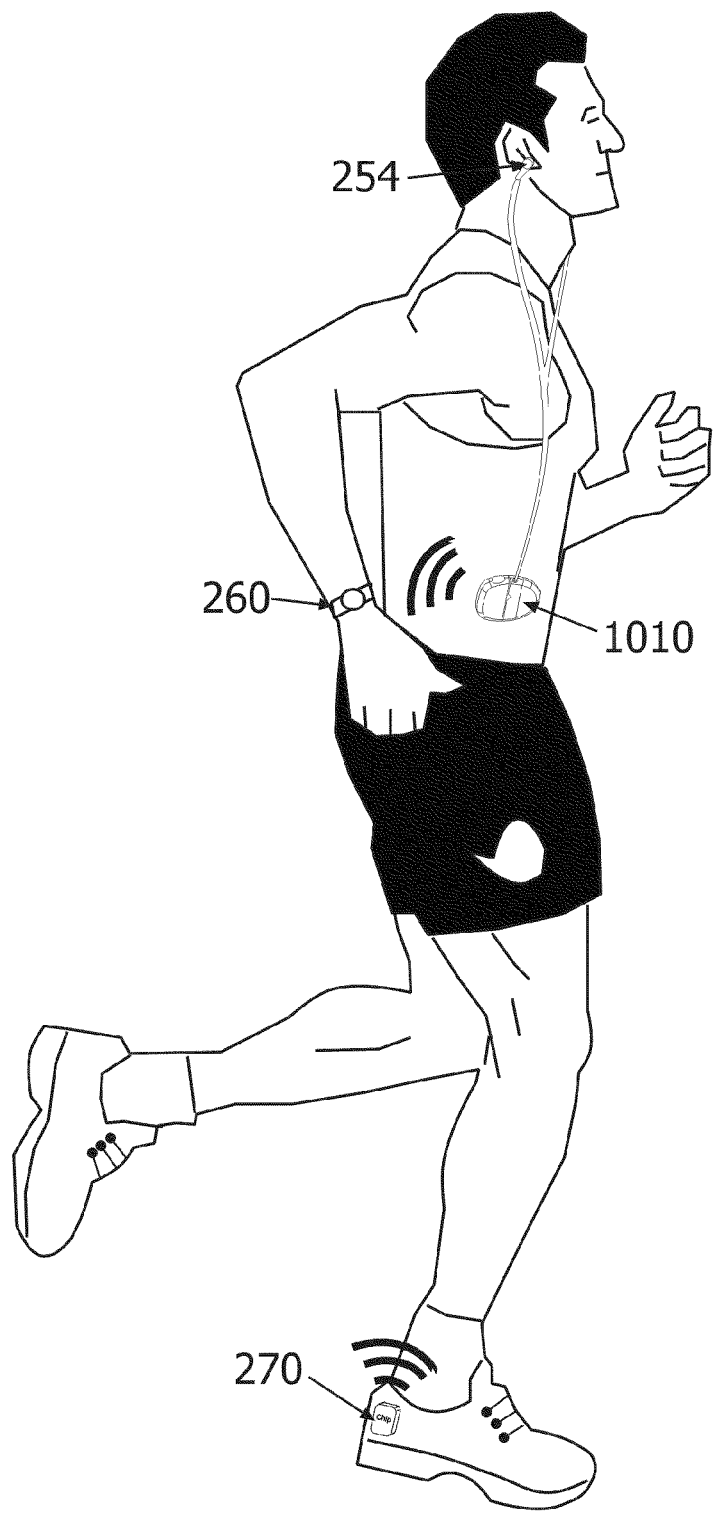
FIGS. 15a-b illustrate an insulin dispensing device that can communicate with a sneaker-based sensor.
Figure 15B:
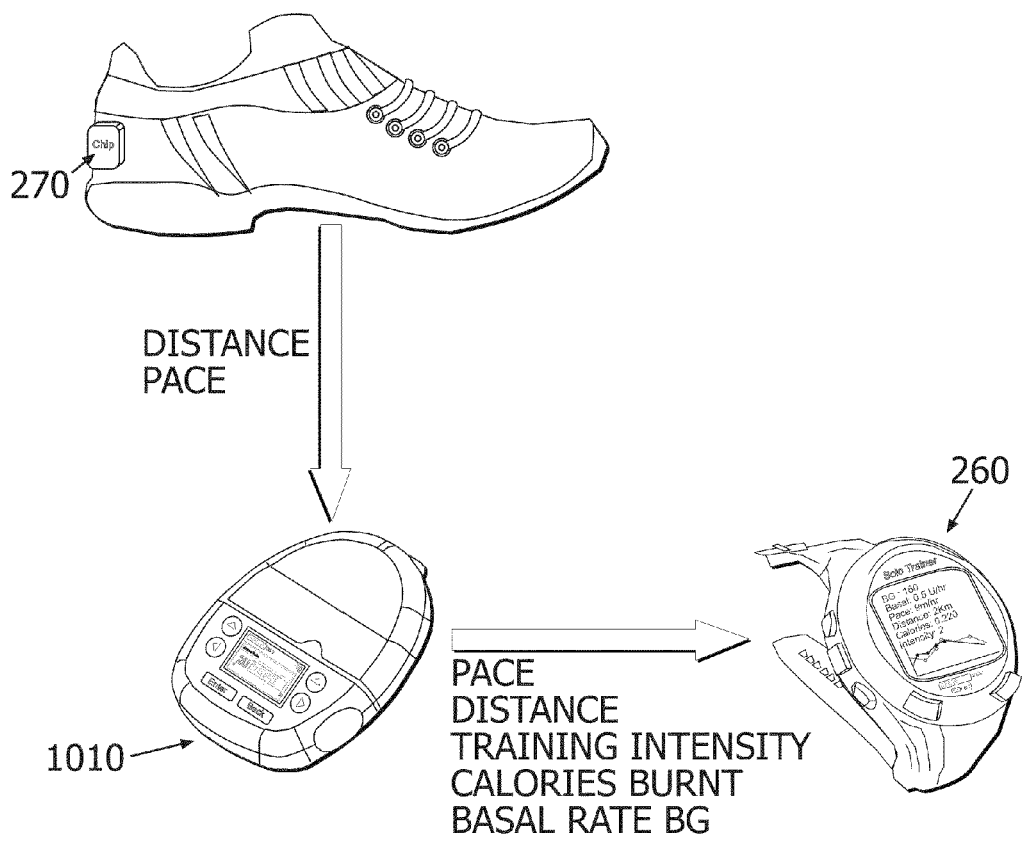

FIG. 15a shows a user with the skin secured patch unit of the insulin dispensing device 1010, a sneaker-based sensor 270, a watch display 260, and earphones 254. FIG. 15b shows the sneaker-based sensor 270, the patch unit of the insulin dispensing device 1010, and the display watch 260 in more detail.

Figure 16:
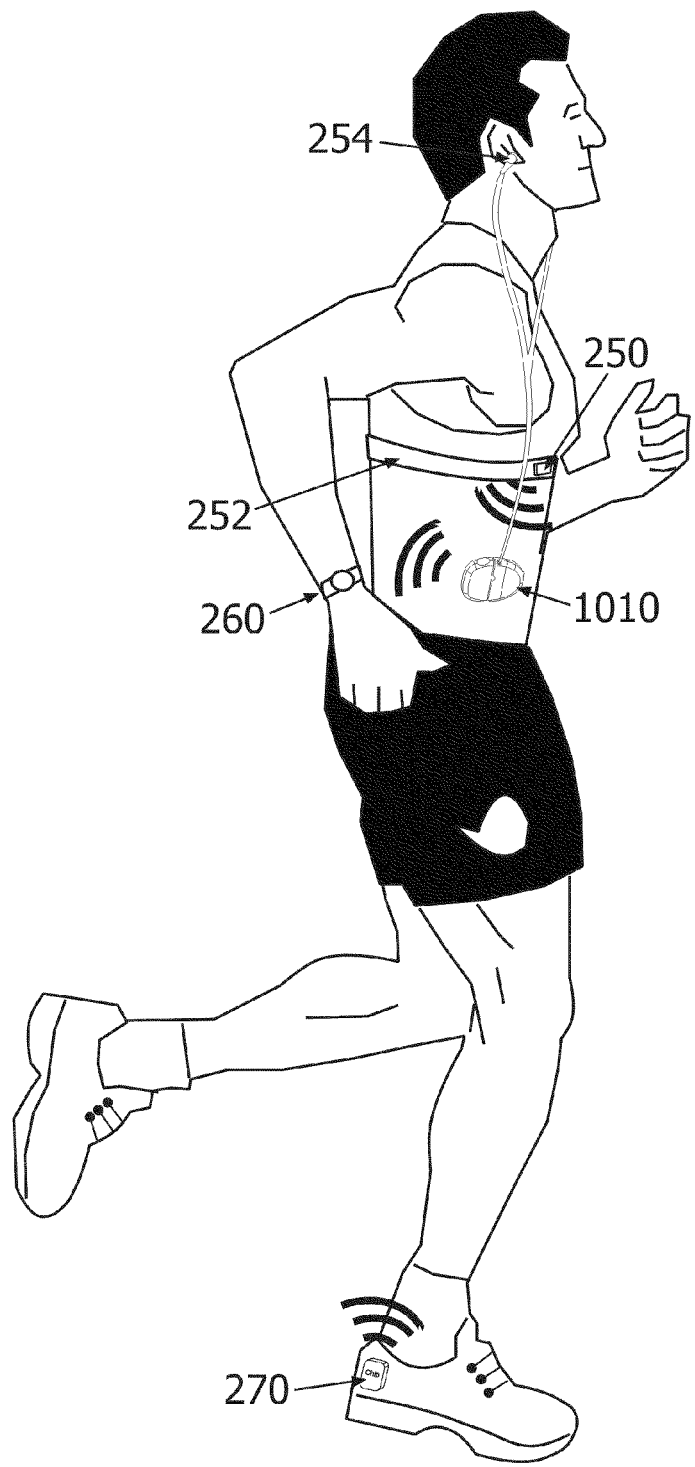
FIG. 16 illustrates an insulin dispensing device that can communicate with a sneaker-based sensor and a heart rate monitor.

FIG. 16 depicts a system that can include an insulin dispensing device 1010. Specifically, FIG. 16 illustrates a user with the skin secured patch unit of the insulin dispensing device 1010, a sneaker-based sensor 270, a heart rate monitor 250 strapped around the user's chest with a belt 252, a watch display 260, and earphones 254.

The insulin dispensing device 1010 can communicate with a sneaker-based sensor 270 and a heart rate monitor 250. In some embodiments, the basal rate can be determined according to the intensity level that matches the sensed HR. The relationship between the pace, as sensed by the sneaker-based sensor 270, and the HR, as sensed by the heart rate monitor 250 can reflect the training status of the user. For example, as the user gets more trained, a lower heart rate can be reached by increasing running (or walking) pace. That is, a certain pace may initially be considered very hard intensity (e.g. 90% maximum HR) and later be moderately hard intensity (e.g. 70% maximum HR). The data integrated, from the three communicating devices (pump, sneaker-based sensor, and HR monitor), such as the training status of the user, may be displayed to the user graphically or non-graphically.

Figure 17C:
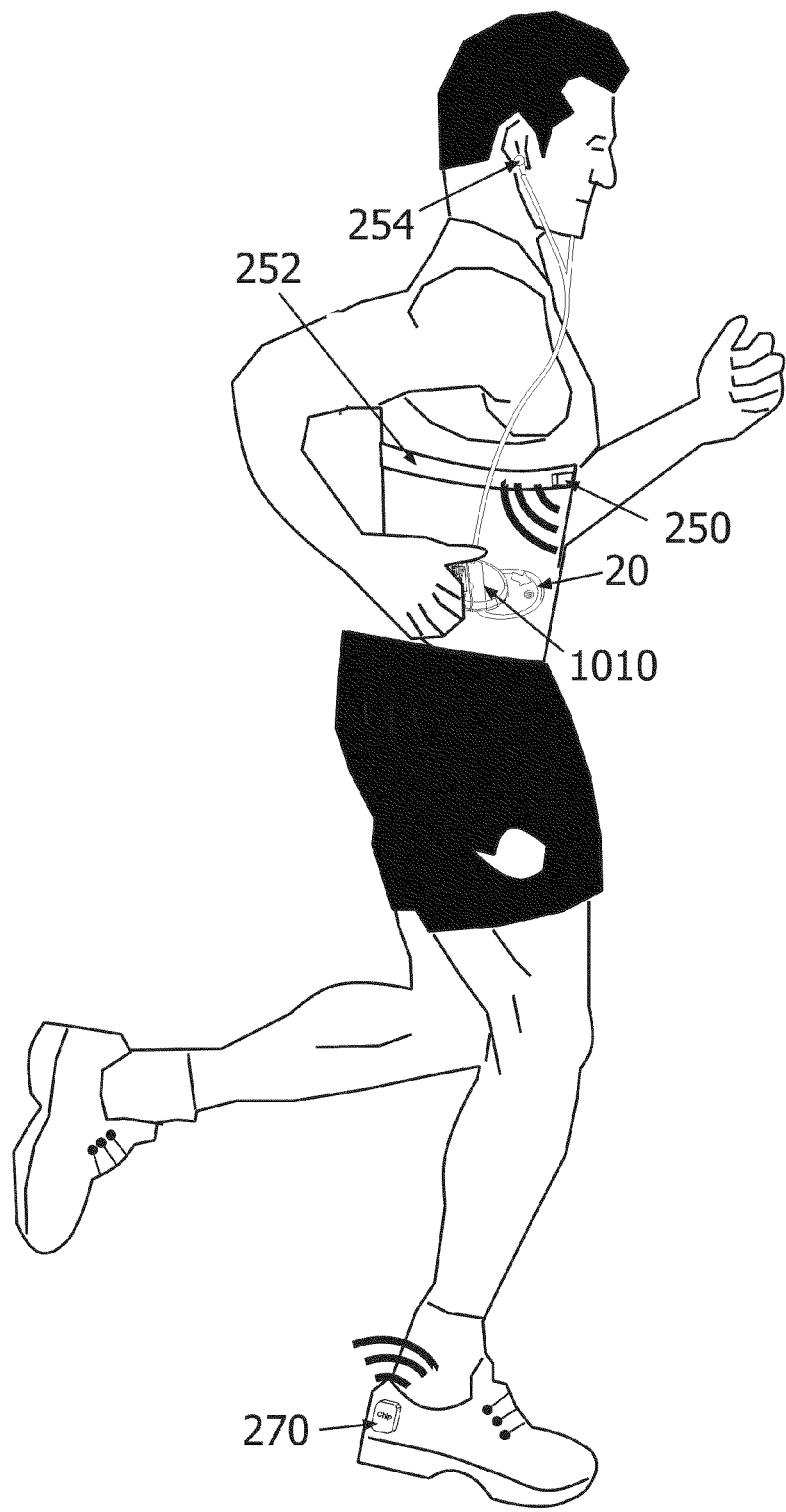

FIGS. 17a-c illustrate a system that can include an insulin dispensing device 1010. The insulin dispensing device 1010 can communicate with a sneaker-based sensor 270 and/or a heart rate monitor 250. The insulin dispensing device 1010 can include a display 214 and be connected and disconnected from a skin adhered cradle unit 20 based on the user's discretion. FIG. 17a shows a user disconnecting the insulin dispensing device 1010 from the cradle unit 20 to view the graphical and/or non-graphical data regarding the exercise and/or pump activity on the screen 214 located on the insulin dispensing device 1010. FIG. 17b shows the insulin dispensing device 1010, with its display 214 and operating buttons 212 in more detail. FIG. 17c shows a user reconnecting the insulin dispensing device 1010 to the cradle unit 20 after viewing the graphical and/or non-graphical data regarding the exercise and/or pump activity on a screen 214 located on the insulin dispensing device 1010.

Figure 18A:
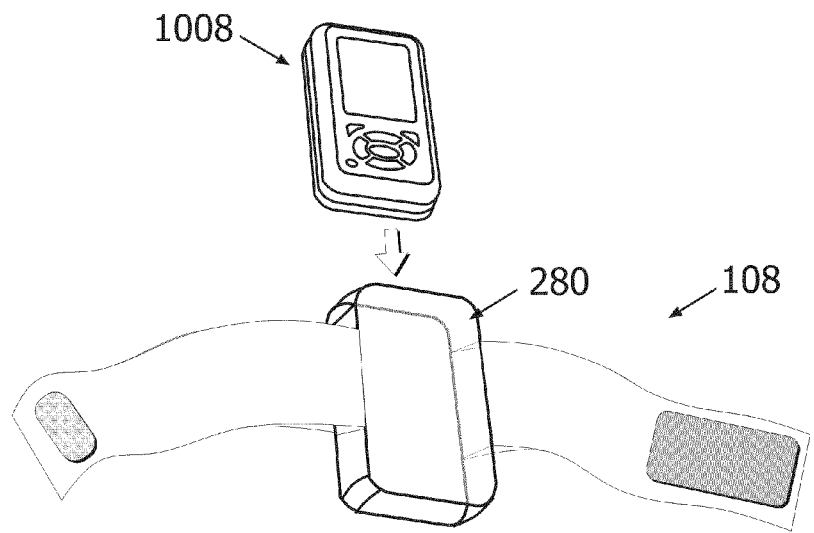
FIGS. 18a-b illustrate an insulin dispensing device with an arm strap.
Figure 18B:
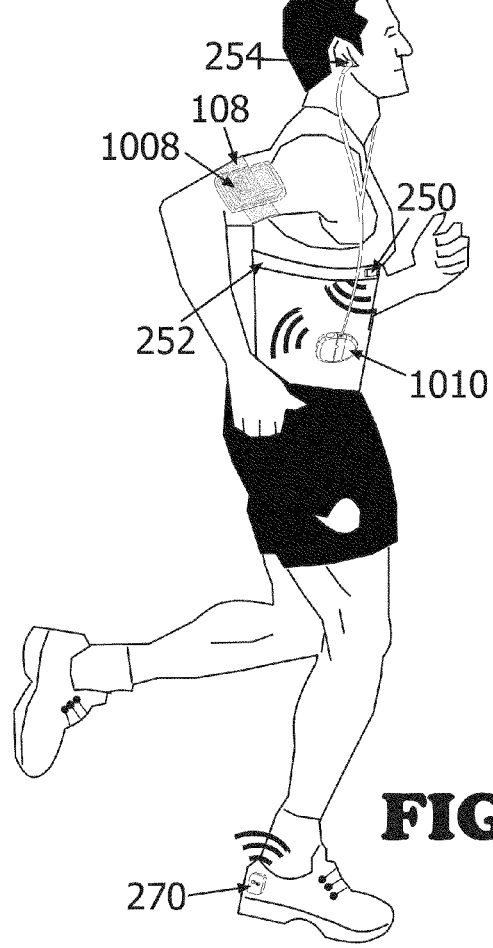

FIGS. 18a-b illustrate a system that can include an insulin dispensing device 1010. The insulin dispensing device 1010 can communicate with a sneaker-based sensor 270 and/or a heart rate monitor 250, wherein the remote control unit 1008 of the insulin dispensing device can be carried by the user in a dedicated arm strap 108. The remote control unit can comprise a display that can show graphical and/or non-graphical data regarding the exercise and/or pump activity. In addition, programming of the insulin dispensing device 1010 can be performed during an exercise through the accessible RC unit 1008.

Figure 19A:
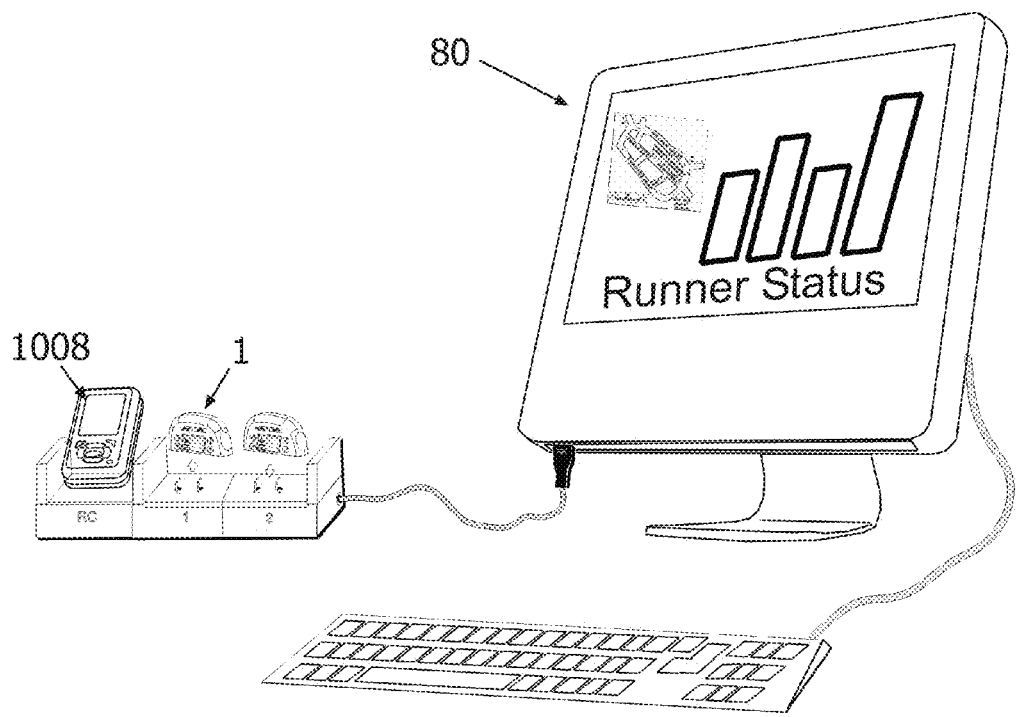
FIGS. 19a-b illustrate insulin delivery devices that can communicate with a PC.
Figure 19B:
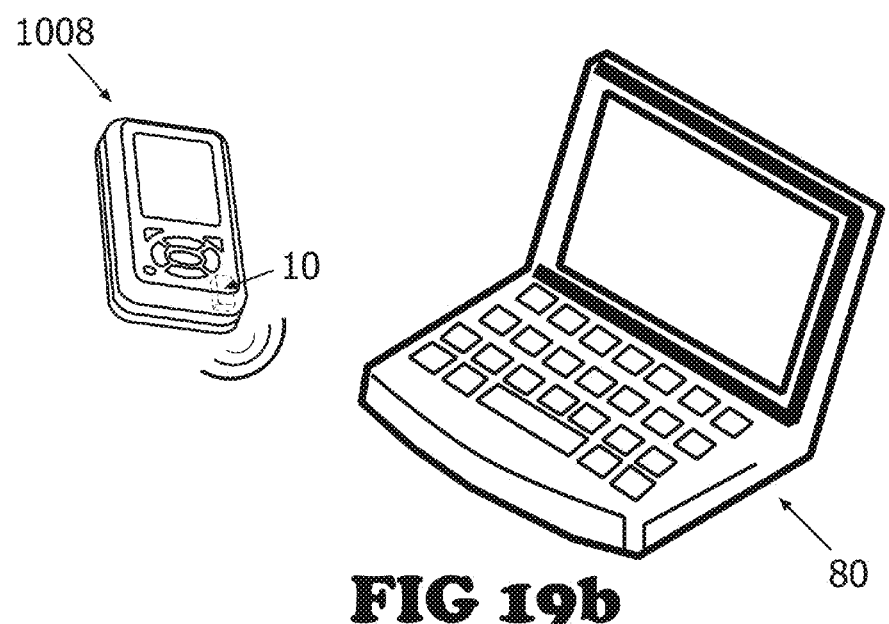

FIGS. 19 a-b show another exemplary system that can include insulin delivery device where the exercise glycemic control feature 10 can communicate with an external PC 80. The exercise glycemic control feature 10 can be located in a remote control unit 1008 or in the reusable part of the patch unit 1. For example, any data derived from the exercise glycemic control feature, including exercise parameters received from adjunctive devices such as a sneaker-based sensor and heart rate monitor, can be saved and can be displayed in any graphical or non-graphical manner. In some embodiments, the saved data can automatically be sent to the patient's doctor or any other medical practitioner (e.g., by electronic mail or any other means) for evaluation, validation or any other clinical intervention. The communication can be hard wired, as shown in FIG. 19a, or wireless, as shown in FIG. 19b.

Figure 20A:
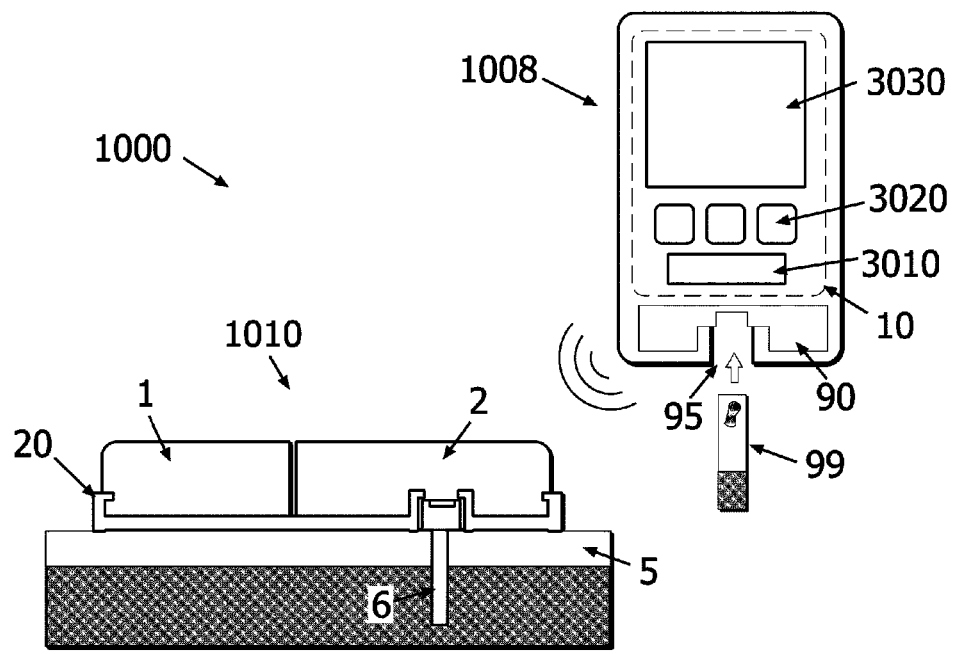
FIGS. 20a-d illustrate insulin delivery device having blood glucose monitors deployed in three different locations providing blood glucose (BG) readings for the exercise glycemic control feature.

FIGS. 20a-d illustrate four exemplary systems that can include the insulin delivery device, each containing a glucometer 90. The glucometer 90 can be used for acquiring blood glucose (BG) values inputted to the exercise glycemic control feature 10. FIG. 20a illustrates a glucometer 90 located in the remote control unit 1008 of the device. In this embodiment, the glucometer 90 can include an opening 95 for receiving of a test strip 99. The patient can extract blood from the body, place a blood drop on the test strip 99 and insert the test strip into the opening 95. The glucose readings can be displayed on a screen 80 of the remote control unit 1008.

Figure 20B:
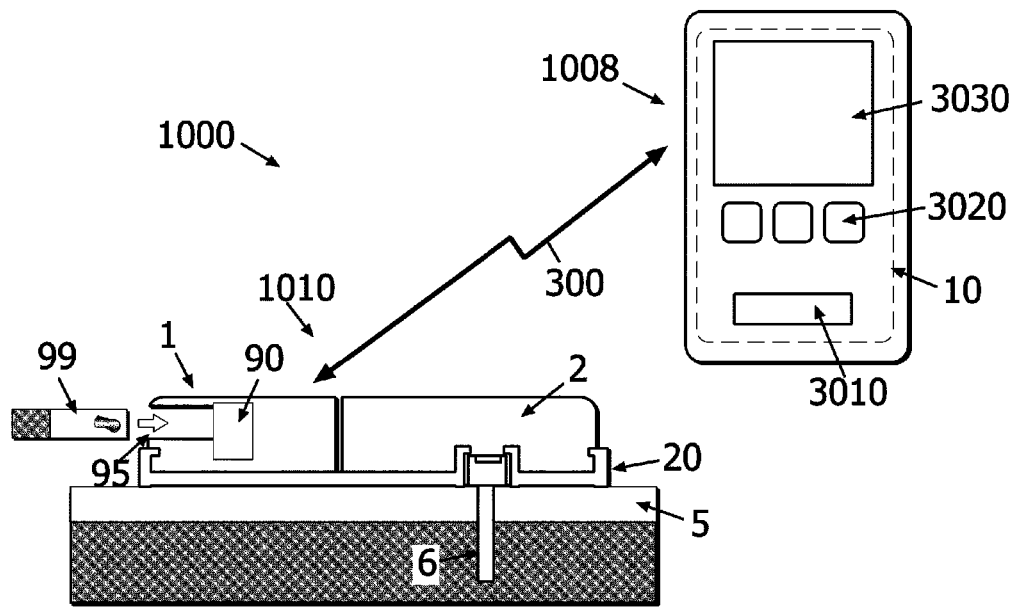
Figure 20C:
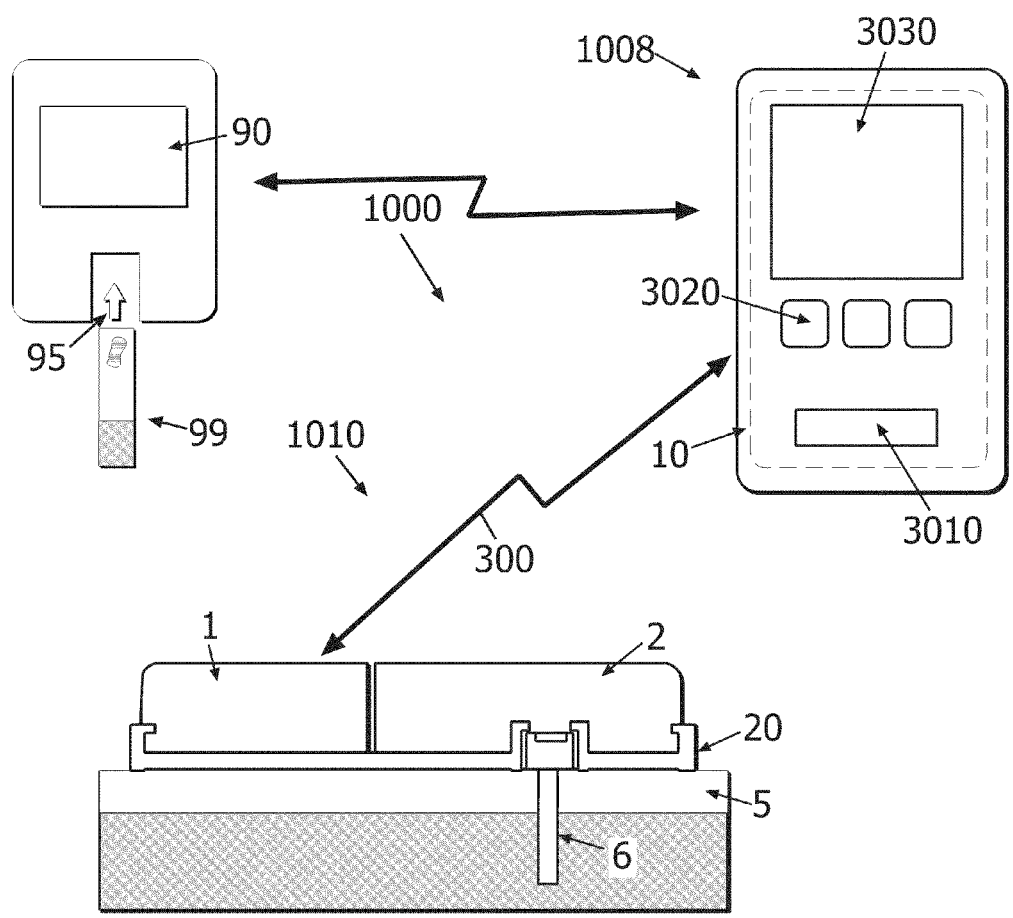
Figure 20D:
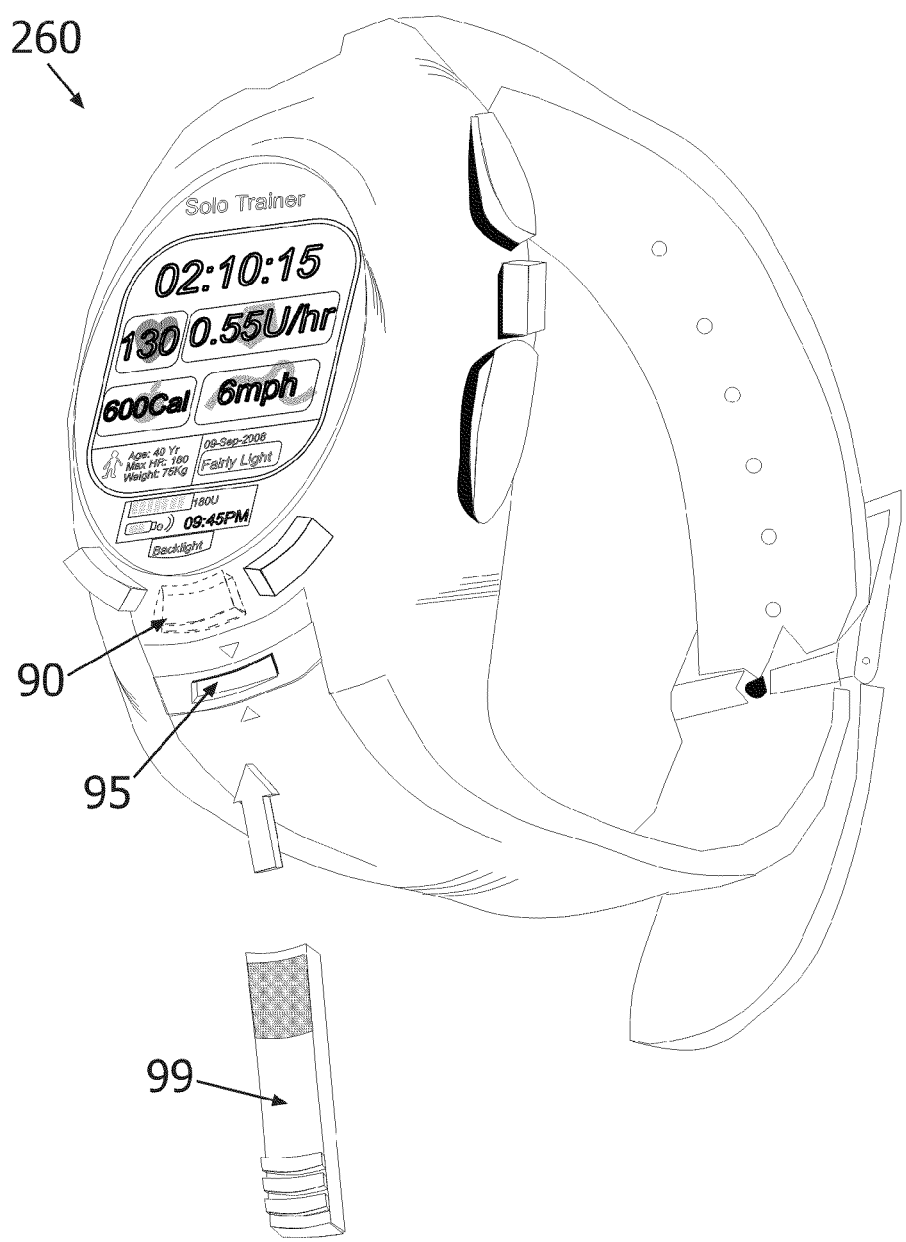

FIG. 20b illustrates a glucometer 90 located in the reusable part 1 of the patch unit 1010. A communication channel 300 may be established to connect the glucometer 90 residing in the patch unit 1010 and the exercise glycemic control feature 10 residing in the remote control unit 1008. The communication channel can be configured to allow programming, data handling, and user inputs. FIG. 20c illustrates an exemplary device in which glucose readings are received from an independent glucometer. FIG. 20d illustrates an exemplary embodiment in which glucose readings can be received from a glucometer located in a display watch 260. Other embodiments are within the scope of the following claims.

Various implementations of the subject matter described herein may be realized in digital electronic circuitry, integrated circuitry, specially designed ASICs (application specific integrated circuits), computer hardware, firmware, software, and/or combinations thereof. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and may be implemented in a high-level procedural and/or object-oriented programming language, and/or in assembly/machine language. As used herein, the term "machine-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the subject matter described herein may be implemented on a computer having a display device (e.g., a CRT (cathode ray tube) or LCD (liquid crystal display) monitor) for displaying information to the user and a keyboard and a pointing device (e.g., a mouse or a trackball) by which the user may provide input to the computer. Other kinds of devices may be used to provide for interaction with a user as well; for example, feedback provided to the user may be any form of sensory feedback (e.g., visual feedback, auditory feedback, or tactile feedback); and input from the user may be received in any form, including acoustic, speech, or tactile input.

The subject matter described herein may be implemented in a computing system that includes a back-end component (e.g., as a data server), or that includes a middleware component (e.g., an application server), or that includes a front-end component (e.g., a client computer having a graphical user interface or a Web browser through which a user may interact with an implementation of the subject matter described herein), or any combination of such back-end, middleware, or front-end components. The components of the system may be interconnected by any form or medium of digital data communication (e.g., a communication network). Examples of communication networks include a local area network ("LAN"), a wide area network ("WAN"), and the Internet.

The computing system may include clients and servers. A client and server are generally remote from each other and typically interact through a communication network. The relationship of client and server arises by virtue of computer programs running on the respective computers and having a client-server relationship to each other.

The methods described herein can be implemented by a set of computer instructions embedded in a computer-readable media. For example, the computer readable media can represent a storage device that can permanently or temporarily store computer readable data. In some implementations, the device can be in a form of a computer disc (e.g. CD, DVD, Blue Ray), a computer hard drive (e.g. disk based drives with moving parts) or a flash drive (e.g. storage device without any moving parts).

Although a few variations have been described in detail above, other modifications are possible. For example, the logic flow depicted in the accompanying figures and described herein does not require the particular order shown, or sequential order, to achieve desirable results. Other implementations may be within the scope of the following claims.

What is claimed is:

1. A computer-implemented method for modifying insulin basal rate delivery to adapt to a user's exercise activity, comprising:
   receiving a first value corresponding to a first glucose concentration before an exercise activity of a user;
   receiving a second value corresponding to a second glucose concentration after the exercise activity of the user;
   determining a glucose concentration change based on a difference between the second value and the first value;
   modifying a basal rate based on a comparison of the glucose concentration change with a predetermined threshold value;
   advising the user to consume carbohydrates if the modified basal rate is insufficient to compensate for the exercise activity;
   determining a recommended amount of carbohydrates wherein the modified basal rate is set to a minimum, and the recommended amount of carbohydrates is determined by calculating:

$$\text{Carb} = \text{CIR} * [(\text{Basal}_{min} * t_{exercise}) + (\Delta/\text{IS}*T)) * t_{exercise} - \text{Basal} * t_{exercise}]$$

wherein:
   Carb represents the recommended amount of carbohydrates,
   CIR represents the user's carbohydrate to insulin ration,
   $\text{Basal}_{min}$ represents the minimum basal rate,
   $t_{exercise}$ represents an exercise parameter associated with the exercise activity,
   $\Delta$ represents the glucose concentration change,
   IS represents the user's insulin sensitivity,
   T represents a duration of the exercise activity, and
   Basal represents the user's basal rate;
   delivering insulin to the body of the user according to the modified basal rate; and
   wherein at least one of receiving the first value, receiving the second value, determining, advising, and modifying is performed by one or more computer processors.

2. The computer-implemented method of claim 1, further comprising:
   receiving first data corresponding to the exercise activity; and
   recording, in a memory, information relating the received first data corresponding to the exercise activity to data representative of the modified basal rate determined for the exercise activity.

3. The computer-implemented method of claim 2, further comprising:
   receiving second data corresponding to another exercise activity;
   retrieving from memory, based on the received second data, data representative of another modified basal rate determined for the other exercise activity, the data representative of the other modified basal rate being related to the other exercise activity using another recorded information; and
   changing the delivering so as to deliver insulin to the body of the user according to the retrieved data representative of the other modified basal rate.

4. The computer-implemented method of claim 2, further comprising:
   reducing the basal rate prior to the exercise activity based on a change basal factor corresponding to the received first data.

5. The computer-implemented method of claim 4, wherein modifying the basal rate comprises decreasing the basal rate by (basal−X*basal)−Δ/(IS*T) based on a determination that the glucose concentration change is greater than the predetermined threshold value, wherein
   Δ represents the glucose concentration change,
   IS represents insulin sensitivity of the user,
   T represents a duration of the exercise activity,
   X represents the change basal factor, and
   basal represents the basal rate.

6. The computer-implemented method of claim 4, wherein modifying the basal rate further comprises increasing the basal rate by (basal−X*basal)+|Δ|/(IS*T) based on a determination that the glucose concentration change is less than a negative of the predetermined threshold value, wherein
   Δ represents the glucose concentration change,
   IS represents insulin sensitivity of the user,
   T represents a duration of the exercise activity,
   X represents the change basal factor, and
   basal represents the basal rate.

7. The computer-implemented method of claim 2, wherein at least a portion of the first data is selected based on one or more physiological parameters of the user.

8. The computer-implemented method of claim 7, wherein the one or more physiological parameters correspond to at least one of: a heart rate, a ventilation rate, a body temperature, steps of the user per period of time.

9. The computer-implemented method of claim 2, wherein the first data corresponds to a Borg scale.

10. The computer-implemented method of claim 1, wherein modifying the basal rate comprises decreasing the basal rate by $$\frac{\Delta}{IS*T}$$

for insulin delivery to the user based on a determination that the glucose concentration change in the user is greater than the predetermined threshold value, wherein:

Δ represents the glucose concentration change,
IS represents insulin sensitivity of the user, and
T represents a duration of the exercise activity.

11. The computer-implemented method of claim 1, wherein modifying the basal rate comprises increasing the basal rate by |Δ|/(IS*T) based on a determination that the glucose concentration change is less than a negative of the predetermined threshold value, wherein Δ represents the glucose concentration change,
IS represents insulin sensitivity of the user, and
T represents a duration of the exercise activity.

12. The computer-implemented method of claim 1, further comprising instructing the user to fast prior to the exercise activity.

13. The computer-implemented method of claim 1, wherein modifying the basal rate is based on one or more user-specific factors selected from the group consisting of: IS, TBG, CIR, RI, and duration of the exercise activity, where IS represents insulin sensitivity of the user, TBG represents the target blood glucose levels of the user, CIR represents the carbohydrate-to-insulin ratio corresponding to the amount of carbohydrate balanced by one unit of insulin, and RI is the residual insulin of the user.

14. The computer-implemented method of claim 1, further comprising:
modifying the basal rate upon termination of the exercise activity based on a predetermined configuration, the predetermined configuration selected from at least one of: a basal rate prior to the exercise activity, a basal rate preprogrammed by the user, and a new basal rate manually selected by the user after the exercise activity.

15. The computer-implemented method of claim 1, further comprising:
providing a recommendation to the user corresponding to a food adjustment based on the glucose concentration change.

16. The computer-implemented method of claim 1, further comprising:
presenting the modified basal rate to the user in a form of at least one of: a percent of the basal rate prior to the modification and a number of units of insulin.

17. A computer-implemented method for modifying insulin basal rate delivery to adapt to a user's exercise activity, comprising:
receiving a first value corresponding to a first glucose concentration before an exercise activity of a user;
receiving a second value corresponding to a second glucose concentration after the exercise activity of the user;
determining a glucose concentration change based on a difference between the second value and the first value;
modifying a basal rate based on a comparison of the glucose concentration change with a predetermined threshold value;
advising the user to consume carbohydrates if the modified basal rate is insufficient to compensate for the exercise activity;
determining a recommended amount of carbohydrates wherein the recommended amount of carbohydrates is determined by calculating:

Carb=(RI$_{activity}$*CIR)−($t_{activity}$*Basal'*CIR)

wherein:
Carb represents the recommended amount of carbohydrates,
RI$_{activity}$ represents the user's residual insulin at the exercise activity's initiation,
CIR represents the user's carbohydrate to insulin ration,
$t_{activity}$ represents an exercise parameter associated with the exercise activity, and
Basal' represents the user's exercise basal rate;
delivering insulin to the body of the user according to the modified basal rate; and
wherein at least one of receiving the first value, receiving the second value, determining, advising, and modifying is performed by one or more computer processors.

18. The computer-implemented method of claim 17, further comprising:
receiving first data corresponding to the exercise activity; and
recording, in a memory, information relating the received first data corresponding to the exercise activity to data representative of the modified basal rate determined for the exercise activity.

19. The computer-implemented method of claim 18, further comprising:
receiving second data corresponding to another exercise activity;
retrieving from memory, based on the received second data, data representative of another modified basal rate determined for the other exercise activity, the data representative of the other modified basal rate being related to the other exercise activity using another recorded information; and
changing the delivering so as to deliver insulin to the body of the user according to the retrieved data representative of the other modified basal rate.

20. The computer-implemented method of claim 18, further comprising:
reducing the basal rate prior to the exercise activity based on a change basal factor corresponding to the received first data.

21. The computer-implemented method of claim 20, wherein modifying the basal rate comprises decreasing the basal rate by (basal−X*basal)−Δ/(IS*T) based on a determination that the glucose concentration change is greater than the predetermined threshold value, wherein Δ represents the glucose concentration change,
IS represents insulin sensitivity of the user,
T represents a duration of the exercise activity,
X represents the change basal factor, and
basal represents the basal rate.

22. The computer-implemented method of claim 20, wherein modifying the basal rate further comprises increasing the basal rate by (basal−X*basal)+|Δ|/(IS*T) based on a determination that the glucose concentration change is less than a negative of the predetermined threshold value, wherein Δ represents the glucose concentration change,
IS represents insulin sensitivity of the user,
T represents a duration of the exercise activity,
X represents the change basal factor, and
basal represents the basal rate.

23. The computer-implemented method of claim 18, wherein at least a portion of the first data is selected based on one or more physiological parameters of the user.

24. The computer-implemented method of claim 23, wherein the one or more physiological parameters correspond to at least one of: a heart rate, a ventilation rate, a body temperature, steps of the user per period of time.

25. The computer-implemented method of claim 18, wherein the first data corresponds to a Borg scale.

26. The computer-implemented method of claim 17, wherein modifying the basal rate is based on one or more user-specific factors selected from the group consisting of: IS, TBG, CIR, RI, and duration of the exercise activity, where IS represents insulin sensitivity of the user, TBG represents the target blood glucose levels of the user, CIR represents the carbohydrate-to-insulin ratio corresponding to the amount of carbohydrate balanced by one unit of insulin, and RI is the residual insulin of the user.

27. The computer-implemented method of claim 17, further comprising:
    modifying the basal rate upon termination of the exercise activity based on a predetermined configuration, the predetermined configuration selected from at least one of: a basal rate prior to the exercise activity, a basal rate preprogrammed by the user, and a new basal rate manually selected by the user after the exercise activity.

28. The computer-implemented method of claim 17, further comprising:
    providing a recommendation to the user corresponding to a food adjustment based on the glucose concentration change.

29. The computer-implemented method of claim 17, further comprising:
    presenting the modified basal rate to the user in a form of at least one of: a percent of the basal rate prior to the modification and a number of units of insulin.

30. The computer-implemented method of claim 17, wherein modifying the basal rate comprises decreasing the basal rate by $$\frac{\Delta}{IS * T}$$

for insulin delivery to the user based on a determination that the glucose concentration change in the user is greater than the predetermined threshold value, wherein:
    $\Delta$ represents the glucose concentration change,
    IS represents insulin sensitivity of the user, and
    T represents a duration of the exercise activity.

31. The computer-implemented method of claim 17, wherein modifying the basal rate comprises increasing the basal rate by $|\Delta|/(IS*T)$ based on a determination that the glucose concentration change is less than a negative of the predetermined threshold value, wherein
    $\Delta$ represents the glucose concentration change,
    IS represents insulin sensitivity of the user, and
    T represents a duration of the exercise activity.

32. The computer-implemented method of claim 17, further comprising instructing the user to fast prior to the exercise activity.

33. A computer-implemented method for modifying insulin basal rate delivery to adapt to a user's exercise activity, comprising:
    receiving a first value corresponding to a first glucose concentration before an exercise activity of a user;
    receiving a second value corresponding to a second glucose concentration after the exercise activity of the user;
    determining a glucose concentration change based on a difference between the second value and the first value;
    modifying a basal rate based on a comparison of the glucose concentration change with a predetermined threshold value;
    advising the user to consume carbohydrates if the modified basal rate is insufficient to compensate for the exercise activity;
    determining a recommended amount of carbohydrates wherein the modified basal rate is set to a minimum, and the recommended amount of carbohydrates is determined by calculating:

$Carb=(RI_{activity}*CIR)-(t_{activity}*Basal'*CIR)+(t_{activity}*Basal_{min}*CIR)$ wherein:
        Carb represents the recommended amount of carbohydrates,
        $RI_{activity}$ represents the user's residual insulin at the exercise activity's initiation,
        CIR represents the user's carbohydrate to insulin ration,
        $t_{activity}$ represents an exercise parameter associated with the exercise activity,
        Basal' represents the user's exercise basal rate, and
        $Basal_{min}$ represents the minimum basal rate;
    delivering insulin to the body of the user according to the modified basal rate; and
    wherein at least one of receiving the first value, receiving the second value, determining, advising, and modifying is performed by one or more computer processors.

34. The computer-implemented method of claim 33, further comprising:
    receiving first data corresponding to the exercise activity; and
    recording, in a memory, information relating the received first data corresponding to the exercise activity to data representative of the modified basal rate determined for the exercise activity.

35. The computer-implemented method of claim 34, further comprising:
    receiving second data corresponding to another exercise activity;
    retrieving from memory, based on the received second data, data representative of another modified basal rate determined for the other exercise activity, the data representative of the other modified basal rate being related to the other exercise activity using another recorded information; and
    changing the delivering so as to deliver insulin to the body of the user according to the retrieved data representative of the other modified basal rate.

36. The computer-implemented method of claim 34, further comprising:
    reducing the basal rate prior to the exercise activity based on a change basal factor corresponding to the received first data.

37. The computer-implemented method of claim 36, wherein modifying the basal rate comprises decreasing the basal rate by $(basal-X*basal)-\Delta/(IS*T)$ based on a determination that the glucose concentration change is greater than the predetermined threshold value, wherein
    $\Delta$ represents the glucose concentration change,
    IS represents insulin sensitivity of the user,
    T represents a duration of the exercise activity,
    X represents the change basal factor, and
    basal represents the basal rate.

38. The computer-implemented method of claim 36, wherein modifying the basal rate further comprises increasing the basal rate by (basal−X*basal)+|Δ|/(IS*T) based on a determination that the glucose concentration change is less than a negative of the predetermined threshold value, wherein Δ represents the glucose concentration change,
IS represents insulin sensitivity of the user,
T represents a duration of the exercise activity,
X represents the change basal factor, and
basal represents the basal rate.

39. The computer-implemented method of claim 34, wherein at least a portion of the first data is selected based on one or more physiological parameters of the user.

40. The computer-implemented method of claim 39, wherein the one or more physiological parameters correspond to at least one of: a heart rate, a ventilation rate, a body temperature, steps of the user per period of time.

41. The computer-implemented method of claim 34, wherein the first data corresponds to a Borg scale.

42. The computer-implemented method of claim 33, wherein modifying the basal rate is based on one or more user-specific factors selected from the group consisting of: IS, TBG, CIR, RI, and duration of the exercise activity, where IS represents insulin sensitivity of the user, TBG represents the target blood glucose levels of the user, CIR represents the carbohydrate-to-insulin ratio corresponding to the amount of carbohydrate balanced by one unit of insulin, and RI is the residual insulin of the user.

43. The computer-implemented method of claim 33, further comprising:

modifying the basal rate upon termination of the exercise activity based on a predetermined configuration, the predetermined configuration selected from at least one of: a basal rate prior to the exercise activity, a basal rate preprogrammed by the user, and a new basal rate manually selected by the user after the exercise activity.

44. The computer-implemented method of claim 33, further comprising:

providing a recommendation to the user corresponding to a food adjustment based on the glucose concentration change.

45. The computer-implemented method of claim 33, further comprising:

presenting the modified basal rate to the user in a form of at least one of: a percent of the basal rate prior to the modification and a number of units of insulin.

46. The computer-implemented method of claim 33, wherein modifying the basal rate comprises decreasing the basal rate by $$\frac{\Delta}{IS*T}$$

for insulin delivery to the user based on a determination that the glucose concentration change in the user is greater than the predetermined threshold value, wherein:

Δ represents the glucose concentration change,
IS represents insulin sensitivity of the user, and
T represents a duration of the exercise activity.

47. The computer-implemented method of claim 33, wherein modifying the basal rate comprises increasing the basal rate by |Δ|/(IS*T) based on a determination that the glucose concentration change is less than a negative of the predetermined threshold value, wherein Δ represents the glucose concentration change,
IS represents insulin sensitivity of the user, and
T represents a duration of the exercise activity.

48. The computer-implemented method of claim 33, further comprising instructing the user to fast prior to the exercise activity.

* * * * *

UNITED STATES PATENT AND TRADEMARK OFFICE
CERTIFICATE OF CORRECTION

PATENT NO. : 9,199,031 B2
APPLICATION NO. : 12/810864
DATED : December 1, 2015
INVENTOR(S) : Yodfat et al.

Page 1 of 1

It is certified that error appears in the above-identified patent and that said Letters Patent is hereby corrected as shown below:

In the claims

Col. 25, Claim 1, Line 64,
"CIR represents the user's carbohydrate to insulin ration," should read
--CIR represents the user's carbohydrate to insulin ratio,--;

Col. 28, Claim 17, Line 12,
"CIR represents the user's carbohydrate to insulin ration," should read
--CIR represents the user's carbohydrate to insulin ratio,--; and Col. 30, Claim 33, Line 22,
"CIR represents the user's carbohydrate to insulin ration," should read
--CIR represents the user's carbohydrate to insulin ratio,--.

Signed and Sealed this
Twenty-first Day of June, 2016

Michelle K. Lee
*Director of the United States Patent and Trademark Office*